United States Patent
Xiao et al.

(10) Patent No.: US 8,642,612 B2
(45) Date of Patent: Feb. 4, 2014

(54) NICOTINIC DESENSITIZERS AND METHODS OF SELECTING, TESTING, AND USING THEM

(75) Inventors: Yingxian Xiao, Potomac, MD (US); Kenneth J. Kellar, Potomac, MD (US)

(73) Assignee: Potomac Pharmaceuticals, Inc., Potomac, MD (US)

( * ) Notice: Subject to any disclaimer, the term of this patent is extended or adjusted under 35 U.S.C. 154(b) by 739 days.

(21) Appl. No.: 12/374,172

(22) PCT Filed: Jul. 18, 2007

(86) PCT No.: PCT/US2007/073814
§ 371 (c)(1),
(2), (4) Date: Feb. 4, 2010

(87) PCT Pub. No.: WO2008/011484
PCT Pub. Date: Jan. 24, 2008

(65) Prior Publication Data
US 2010/0129291 A1    May 27, 2010

Related U.S. Application Data

(60) Provisional application No. 60/831,471, filed on Jul. 18, 2006, provisional application No. 60/836,406, filed on Aug. 9, 2006.

(51) Int. Cl.
*A01N 43/40* (2006.01)
*A61K 31/435* (2006.01)

(52) U.S. Cl.
USPC ....................................................... 514/277

(58) Field of Classification Search
USPC ............................................... 514/219, 277
See application file for complete search history.

(56) References Cited

U.S. PATENT DOCUMENTS

| | | | |
|---|---|---|---|
| 5,308,854 A | * | 5/1994 | Hoffman et al. ............... 514/338 |
| 8,030,300 B2 | * | 10/2011 | Kozikowski et al. ...... 514/210.2 |
| 2008/0132486 A1 | | 6/2008 | Kozikowski et al. |

FOREIGN PATENT DOCUMENTS

WO    WO 2005/000806    *    1/2005

OTHER PUBLICATIONS

Chellappan et al., "Synthesis and Pharmacological Evaluation of Novel 9- and 10-Substituted Cytisine Derivatives, Nicotinic Ligands of Endacned Subtype Selectivity," J. Med. Chem. 49:2673-2676 (2006).

Chong, "International Search Report," 2 pages, PCT appl. No. PCT/US07/73814, United States Patent and Trademark Office (mailed Aug. 29, 2008).

Chong, "Written Opinion," 3 pages, PCT appl. No. PCT/US07/73814, United States Patent and Trademark Office (mailed Aug. 29, 2008).

* cited by examiner

*Primary Examiner* — Yong Chong
(74) *Attorney, Agent, or Firm* — Cooley LLP

(57) ABSTRACT

The present invention discloses nicotinic desensitizers and methods of selecting, testing, and using them. The present invention provides methods for selecting nicotinic desensitizers from one or more compounds by using receptor, cell, and tissue models; and methods for testing one or more nicotinic desensitizers for their therapeutic utility by using animal models. The present invention also provides compounds of formula (I) and (II) as nicotinic desensitizers. Nicotinic desensitizers of the present invention are useful for the treatment of a wide range of conditions, diseases, and disorders.

14 Claims, 3 Drawing Sheets

NICOTINIC DESENSITIZERS AND METHODS OF SELECTING, TESTING, AND USING THEM

CROSS-REFERENCE TO RELATED APPLICATIONS

This application claims priority to U.S. Provisional Application Ser. No. 60/831,471, entitled "Nicotinic Desensitizers and Methods of Selecting, Testing and Using Them", filed Jul. 18, 2006, and U.S. Provisional Application Ser. No. 60/836,406, entitled "Nicotinic Desensitizers and Methods of Selecting, Testing and Using Them", filed Aug. 9, 2006. The content of these provisional applications are herein incorporated by reference in their entirety for all purposes.

FEDERALLY FUNDED RESEARCH

The present invention was made at least partly with the U.S. government support under DA-06486, DA-12976, DA-17980, and DA-13199 awarded by the National Institute of Health (NIH). The U.S. government may therefore have certain rights in this invention.

FIELD OF THE INVENTION

The present invention relates to nicotinic desensitizers, a new class of nicotinic acetylcholine receptor ligands, and methods of selecting, testing, and using them.

BACKGROUND OF THE INVENTION

Nicotinic acetylcholine receptors (nAChRs) are members of the Cys-loop superfamily of receptor-coupled ion channels (Karlin, 2002; Kellar and Xiao, 2007; Lester et al., 2004; Sine and Engel, 2006). The superfamily includes, for example, muscle nAChRs, neuronal nAChRs, 5-hydroxytryptamine type 3 (5-$HT_3$) receptors, γ-aminobutyric acid type A ($GABA_A$) and $GABA_C$ receptors and glycine receptors. Neuronal nAChRs are differentially expressed in many regions of the central nervous system (CNS) and peripheral nervous system (PNS) (Alkondon and Albuquerque, 2004; Kellar et al., 1999; Le Novere et al., 2002; Lukas et al., 1999; Paterson and Nordberg, 2000; Skok, 2002).

Neuronal nAChRs are fundamental to many physiological functions of the CNS and PNS. In brain, nAChRs modulate the release of major CNS neurotransmitters, including dopamine (DA), norepinephrine, acetylcholine (ACh), γ-aminobutyric acid (GABA) and glutamate, which are associated with arousal, reward, mood and affect, attention, learning and memory (Dani and Bertrand, 2007; Levin et al., 2006; Wonnacott et al., 2006). In PNS, neuronal nAChRs mediate fast neurotransmission provided by ACh at virtually all autonomic ganglia, sensory ganglia and adrenal gland (De Biasi, 2002; Wang et al., 2002).

These receptors are implicated in many pathological conditions and processes, including aging, addiction, pain, obesity, schizophrenia, epilepsy, mania and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, amyotrophic lateral sclerosis, inflammation, stoke and spinal-cord injury (Gotti and Clementi, 2004; Lindstrom, 1997).

nAChRs also mediate the pharmacological effects of exogenous nicotinic ligands, such as nicotine, lobeline, hexamethonium and mecamylamine (Daly, 2005; Jensen et al., 2005). Moreover, these receptors mediate the effects of nicotine, the addictive agent in tobacco (Laviolette and van der Kooy, 2004; Mansvelder and McGehee, 2002) and the main reason that more than one billion people worldwide smoke.

Neuronal nAChRs are pentameric membrane proteins composed of five subunits. To date, nine α subunits (α2-α10) and three β subunits (β2-(β4) have been found in vertebrates (Le Novere et al., 2002; Lindstrom, 1996; Millar, 2003). Different combinations of these α and β subunits define nAChR subtypes. Although the theoretical number of potential subtypes is very large, a much smaller number of native nAChR subtypes that represent the majority of neuronal nAChRs, including two heteromeric subtypes, α4β2 and α3β4, and one homomeric subtype, α7. In most areas of mammalian brain, the α4β2 subtype represents the predominant population of nAChRs; in ganglia, however, α3β4 nAChRs are the major subtype (Flores et al., 1996; Flores et al., 1992; Gotti et al., 2006; Paterson and Nordberg, 2000; Skok, 2002; Whiting and Lindstrom, 1987).

The nAChRs have been objects on interest for more than 100 years (Langley, 1907). It has been known for many years that ACh, the endogenous agonist, and nicotine, the classical ligand that defines nAChRs, change the functional states of nAChRs. Initially, application of the ligands allows conduction of $Na^+$, $K^+$ and $Ca^{2+}$ ions, which can lead to membrane depolarization and altered cell function. However, if ACh or nicotine is continuously applied, nAChRs quickly become unresponsive to the presence of the ligands, temporarily stopping conduction of the cations. It is an obviously fortunate property of this agonist-receptor system to cells; otherwise, an agonist may cause the channels to be open too long, which would likely interfere with normal cell functions and eventually may even lead to cell death (Gahring and Rogers, 2005).

Many mechanisms and models have been proposed to explain the complex relationship between nAChRs and their ligands. Though far from complete, the following simplified model is widely accepted by researchers in the field. nAChRs are allosteric proteins that respond to the action of ACh at the binding site by changing the status of the channel gate to carry out the function of the nAChR (Changeux and Edelstein, 1998; Changeux and Edelstein, 2005; Colquhoun and Sakmann, 1998; Hogg and Bertrand, 2007; Sine and Engel, 2006; Unwin, 2005). The receptors have at least three discrete conformational states: a resting state (closed), an open state (opened) and a desensitized state (closed) (Karlin, 1967; Karlin, 2002; Katz and Thesleff, 1957). A particular nicotinic ligand, such as ACh, has a certain affinity for each of the three states. In the absence of bound ligand, nAChRs fluctuate among all three conformational states, but most of the time they are in the resting state. The binding of a ligand to a certain state of the receptor increases the probability of the receptor to be in that state. For example, an agonist binds with a reasonably high affinity to the open state of a receptor, and thus increases the probability of it being in the open (active) conformational state. For a population of receptors, the overall initial effect of the agonist is to shift a certain subpopulation of receptors from the resting state to the open state. In the open state, cations flow through the channel. However, the agonist has an even higher affinity for the desensitized state of the receptor; therefore, the eventual effect of an agonist is to "drive" receptor population from the resting and open states to the desensitized state, in which receptors remain closed. The kinetic rates for transitions between states vary greatly among different nAChR subtypes, which contribute to the great functional diversity of neuronal nAChRs.

In addition to ACh and nicotine, many other natural products and synthetic compounds act on nAChRs (Cassels et al., 2005; Daly, 2005; Jensen et al., 2005; Paterson and Nordberg, 2000). Nicotinic ligands belong to the following three major classes according to their actions.

(1) Agonists. Nicotinic agonists, such as ACh or nicotine, activate nAChRs leading to the opening of their channels, which allows cations to cross the membrane; but prolonged presence of agonists desensitizes the receptors. The actions can be explained by the three-state model, with some speculations. Agonists have low binding affinity at the resting state of nAChRs, higher affinity at the open state, and highest binding affinity at the desensitized state. After an agonist binds, the transition from the resting state to the open state is fast, but the transition from open state to desensitized state is slow. Therefore, agonists can activate receptors to open their channels initially but if present for an extended period, agonists desensitize receptors to close the channels.

(2) Competitive Antagonists. A competitive antagonist, such as dihydro-β-erythroidine (DHβE), does not activate nAChRs but prevents agonists from activating nAChRs by binding to the ACh site. A possible mechanism is that competitive antagonists have higher binding affinity at the resting state of receptors than at the open state; therefore, they do not increase the probability of the open state but can prevent agonists from binding to the ACh site.

(3) Noncompetitive Antagonists. A noncompetitive antagonist, such as mecamylamine, does not activate nAChRs but prevents an agonist from activating nAChRs by binding to a site different from the ACh site. For example, the binding site for mecamylamine is in the central pore of the receptors, and so it blocks the pathway for ions, preventing the function of an agonist (Bertrand et al., 1990; Webster et al., 1999).

More than 100 years ago, nicotine was found to both stimulate and block responses of autonomic ganglia (Langley, 1905; Langley and Dickenson, 1889). The concept of desensitization of muscle nAChRs was proposed 50 year ago (Katz and Thesleff, 1957). Since then, it has been widely accepted that all nicotinic agonists have the dual actions of activation and desensitization of nAChRs and that all muscle and neuronal nAChR subtypes can be desensitized by agonists (Giniatullin et al., 2005; Jensen et al., 2005; Lindstrom, 2002; Quick and Lester, 2002; Wang and Sun, 2005).

It is obvious that the activation of neuronal nAChRs by ACh is important for physiological functions. For example, the activation of postsynaptic nAChRs is essential for conducting fast neurotransmissions by ACh. But it is not very clear if the desensitization of neuronal nAChRs by ACh plays important roles in physiological functions. In fact, the desensitization of neuronal nAChRs should be very brief and scattered, if it occurs, because ACh released from cells is rapidly hydrolyzed by acetylcholinesterase (Kellar, 2006; Zhou et al., 2002).

Pharmacologically, long lasting desensitization of neuronal nAChRs can be produced by applying acetylcholinesterase inhibitors, or by applying agonists that are not rapidly degraded or removed from the receptor vicinity. Nicotine is not readily degraded in vivo ($t_{1/2}$>1 hour). In a smoker's brain, the nicotine concentration is high enough to desensitize α4β2 nAChRs for prolonged time periods (Brody et al., 2006; Fitch et al., 2003; Ghosheh et al., 2001; Gourley and Benowitz, 1997; Henningfield et al., 1993; Kellar et al., 1999; Kuryatov et al., 2005).

A fundamental question of nicotinic signaling in the CNS is how each of these two opposite actions contributes to the overall pharmacological effects of nicotine. Most studies have focused on the activation of nAChRs to understand nicotine's effects; therefore, there is a rich literature on the activation of nAChRs by nicotine in vitro and in vivo. Since it was conceptualized, there have been concerns that desensitization might be only an experimental phenomenon with minimum physiological or even pharmacological significance (Colquhoun and Sakmann, 1998; Katz and Thesleff, 1957). However, many investigators have recognized that desensitization of the receptors by nicotine plays potentially important roles in nicotine's effects in brain (Gahring and Rogers, 2005; Giniatullin et al., 2005; Kellar et al., 1999; Lu et al., 1999; Quick and Lester, 2002; Wang and Sun, 2005). In rats, for example, a single injection of nicotine initially stimulates prolactin release, but it then blocks subsequent nicotine-stimulated prolactin release for several hours or longer (Hulihan-Giblin et al., 1990; Sharp and Beyer, 1986). To explain this observation, nicotine was proposed to act as a "time-averaged antagonist" of nAChRs (Hulihan-Giblin et al., 1990), meaning that after a brief initial stimulation of brain nAChRs, it causes a long-lasting desensitization of the receptors that prevents their function for an extended period of several hours. This concept, "time-averaged antagonist", indicted that the desensitization of nAChRs might be the predominant mechanism for some of nicotine's in vivo pharmacological effects.

The brain α4β2 nAChRs are implicated in the addictive effects of nicotine (Flores et al., 1992; Marubio et al., 2003; Maskos et al., 2005; Picciotto et al., 1998; Tapper et al., 2004). It is widely accepted that the mesocorticlimbic dopamine system plays a central role in the rewarding effects of drugs (Nestler, 2005); and like many other addictive drugs, nicotine elevates dopamine in the nucleus accumbens (NAc), which is believed to have a vital role in nicotine addiction. Interestingly, a single injection of nicotine in rats elevates the dopamine concentration in NAc for hours (Di Chiara, 2000; Pidoplichko et al., 2004). It is very difficult to explain this long lasting elevation of dopamine only by activation of nAChRs, which is very brief. Similarly, it is very difficult to explain the lasting pleasure and relief felt by smokers after smoking by only nAChR activation. A complex mechanism has been proposed (Dani and Bertrand, 2007; Dani and Harris, 2005), in which nicotine initially causes activation of α4β2 nAChRs on DA neurons, which originate in the ventral tegmental area (VTA) and project to the NAc, leading to elevate DA in the NAc. Then, when the α4β2 nAChRs on DA neurons are desensitized and thus no longer increasing DA release, the α4β2 nAChRs on inhibitory GABAergic interneurons in the VTA are also desensitized, which decreases the inhibitory influence of GABA on the DA neurons in the VTA. Thus, the lasting desensitization of α4β2 nAChRs on inhibitory GABAergic interneurons produces a sustained overall stimulation of DA release in the NAC.

All nicotinic agonists have these dual actions of activation and desensitization. Therefore, it has been very difficult, if not impossible, to determine conclusively how much each of the two actions contributes to the rewarding effects of nicotine and to addiction. However, it is supported by accumulating experimental evidence that desensitization plays very important roles in mediating in vivo effects of nicotine and other nicotinic agonists.

Native subtypes of nAChRs are differently expressed in many regions of the CNS and PNS. These subtypes have characteristic physiological, pathological and pharmacological properties. The attention in developing nicotinic therapeutics has focused on generating agonists (including partial agonists) that activate nAChRs. Clinical targets for these potential nicotinic drugs include cognitive performance, neurodegenerative diseases, schizophrenia, anxiety and depression, Tourette's syntdrome, epilepsy, pain, smoking cessation, ulcerative colitis, and others (Cassels et al., 2005; Daly, 2005; Jensen et al., 2005). Varenicline, a cytisine analog and a partial agonist of α4β2 nAChRs, was approved in 2006 by U.S. Food and Drug Administration for use as a smoking cessation aid (Rollema et al., 2007). However, many nicotinic agonists, including varenicline, have undesirable side effects that eliminated or limited their clinic applications. For example, an initially very promising potential pain medicine, tebanicline (ABT-594), a nicotinic agonist, failed recently in Phase II clinic trails because of strong gastrointestinal adverse effects (Jain, 2004; Jensen et al., 2005). It is believed that the side effects of tebanicline are caused by its strong α3β4 nAChR agonist activity. Moreover, varenicline, the new smoking cessation aid, which is generally viewed as a safe drug, causes nausea in nearly 30% of the clinic trail participants. This side effect of varenicline is, presumably, also caused by its α3β4 nAChR agonist activity (Mihalak et al., 2006). Thus, there is clearly a need to develop new nicotinic therapeutics that have much better pharmacological profiles than those of the nicotinic agonist on the market or under the development.

Citation or identification of any reference in this section and other sections of this application is not an admission that such reference is prior art to the present invention. The content of each and every of the cited references are herein incorporated by reference in their entirety.

SUMMARY OF THE INVENTION

The present invention provides nicotinic desensitizers, a new class of nicotinic acetylcholine receptor ligands, and methods of selecting, testing, and using them. Nicotinic desensitizers are useful for the treatment of a wide range of conditions, diseases, or disorders. Since their pharmacological profile is markedly different from those of classical nicotinic agonists and antagonists, nicotinic desensitizers are therapeutically efficacious with minimal or no side effects that are typically caused by classical nicotinic agonists or antagonists.

In one embodiment, the present application provides a method of screening one or more compounds to identify one or more nicotinic desensitizers. The method comprises identifying a compound as a nicotinic desensitizer if said compound (1) has binding affinity ($K_d$ or $K_i$) less than about 1,000 nM to a nAChR subtype; (2) has agonist activity ($E_{max}$) to the nAChR subtype less than about 10% of the $E_{max}$ of a typical nicotinic agonist to the nAChR subtype; and (3) has potency of inhibiting receptor activation of the nAChR subtype by the typical agonist ($IC_{50(A)}$) more than about 1,000 nM when the compound is applied to the nAChR subtype simultaneously with the typical nicotinic agonist.

In another embodiment, the present invention provides a method of screening one or more compounds to identify one or more nicotinic desensitizers. The method comprises identifying a compound as a nicotinic desensitizer if said compound (1) has agonist activity ($E_{max}$) to a nAChR subtype less than 10% of the $E_{max}$ of a typical nicotinic agonist to the nAChR subtype; (2) has potency of inhibiting receptor activation of the nAChR subtype by the typical nicotinic agonist via desensitization ($IC_{50(D)}$) less than about 10,000 nM; (3) has inhibition of receptor activation of the nAChR subtype by a typical nicotinic agonist ($IC_{50(A)}$) more than 1,000 nM when the compound is applied to the nAChR subtype simultaneously with the typical nicotinic agonist; and (4) the $IC_{50(D)} < $ the $IC_{50(A)}$. The desensitization comprises contacting each of the one or more compounds with the nAChR subtype for a period of time before a typical nicotinic agonist is applied to the nAChR subtype.

In yet another embodiment, the present invention provides a compound of formula (I):

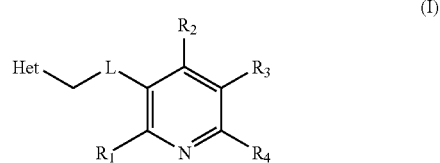

or a pharmaceutically acceptable tautomer, salt, solvate, and/or ester thereof, wherein, L is O, S, or $NR^5$;

Het is heterocyclyl;

each $R^1$, $R^2$, $R^3$, and $R^4$, is independently H, halo, amino, N-alkyl amino, N,N-dialkyl amino, amido, nitro, cyano, hydroxyl, alkoxy, or an optionally substituted $C_1$-$C_{12}$ alkyl, $C_2$-$C_{12}$ alkenyl, or $C_2$-$C_{12}$ alkynyl, wherein the substituents are selected from the group consisting of hydroxyl, halo, amino, N-alkyl amino, N,N-dialkyl amino, —NH—C(O)—$R^6$, —NH—C(O)—$OR^6$, —O—C(O)—$R^6$, —O—C(O)—$OR^6$, nitro, and alkoxy;

$R^5$ is H, or an optionally substituted $C_1$-$C_6$ alkyl, $C_2$-$C_6$ alkenyl, or $C_2$-$C_6$ alkynyl; and $R^6$ is an optionally substituted $C_1$-$C_6$ alkyl, $C_2$-$C_6$ alkenyl, $C_2$-$C_6$ alkynyl, aryl, or heteroaryl.

In yet another embodiment, the present invention provides a compound of formula (II):

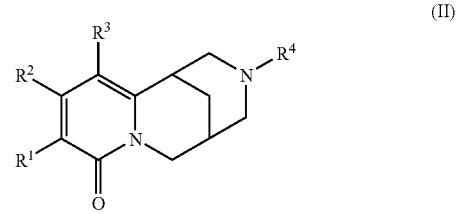

or a pharmaceutically acceptable tautomer, salt, solvate, and/or ester thereof, wherein, $R^1$, $R^2$, and $R^3$ are each independently H, halo, amino, N-alkyl amino, N,N-dialkyl amino, amido, nitro, cyano, hydroxyl, alkoxy, or an optionally substituted $C_1$-$C_6$ alkyl, $C_2$-$C_6$ alkenyl, or $C_2$-$C_6$ alkynyl, wherein the substituents are selected from the group consisting of hydroxyl, halo, amino, nitro, and alkoxy; and $R^5$ is H, an optionally substituted $C_1$-$C_6$ alkyl, $C_2$-$C_6$ alkenyl, or $C_2$-$C_{10}$ alkynyl; wherein the substituents are selected from the group consisting of hydroxyl, halo, amino, nitro, and alkoxy.

In yet another embodiment, the present invention provides a pharmaceutical composition comprising a therapeutically effective amount of at least one nicotinic desensitizer, or a pharmaceutically acceptable salt, solvate, and/or ester thereof; and a pharmaceutically acceptable carrier or excipient. In yet another embodiment, the pharmaceutical composition further comprises at least one additional active agent.

In yet another embodiment, the present invention provides a method for treating, preventing, or reversing one or more conditions or diseases associated with aging, addiction, pain, obesity, schizophrenia: epilepsy, mania and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, amyotrophic lateral sclerosis, inflammation, stoke and spinal-cord injury in a patient suffering said one or more conditions or diseases comprising administering to the patient a therapeutically effective amount of at least one nicotinic desensitizer, or pharmaceutically acceptable salt, solvate, and/or ester thereof. In yet another embodiment, the method further comprises co-administering at least one additional active agent.

DETAILED DESCRIPTION OF THE INVENTION

Figure 1:
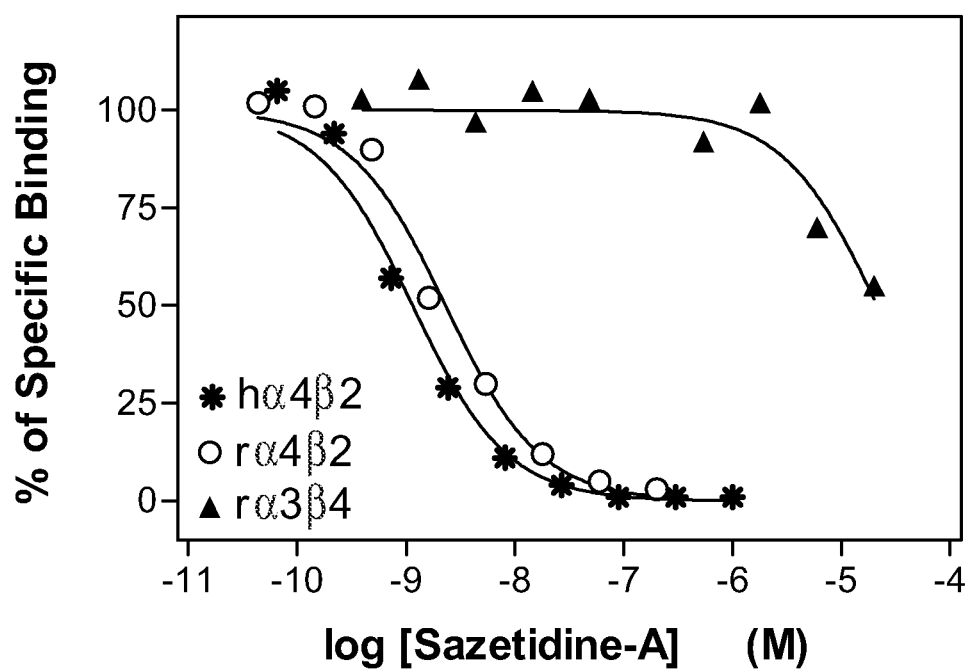
FIG. 1. Competition by sazetidine-A for nAChR binding sites labeled by [$^3$H]epibatidine. Competition binding assays were carried out in SH-EP1 cells expressing human $\alpha 4\beta 2$ nAChRs (h$\alpha 4\beta 2$), or HEK cells expressing rat $\alpha 4\beta 2$ nAChRs (r$\alpha 3\beta 4$) or rat $\alpha 3\beta 4$ nAChRs (r$\alpha 3\beta 4$), as described in Methods. The concentration of [$^3$H]EB used was 100 pM. Data shown are representative of 3 to 5 independent experiments. See Table 1 for a summary of the $K_i$ values for sazetidine-A binding at these receptors.

A nicotinic desensitizer is a ligand that can desensitize a nicotinic acetylcholine receptor (nAChR) but not activate the receptor channel function in a significant manner. By "not activating the receptor channel function in a significant manner", it is meant having agonist activity to a nAChR subtype ($E_{max}$) less than about 10% of the $E_{max}$ of a typical nicotinic agonist. More specifically, a nicotinic desensitizer is a ligand that has one or more of the following characteristics: (1) has high binding affinity to a nicotinic acetylcholine receptor (nAChR) subtype in binding assays; (2) does not have agonist activity to the receptor subtype, or has a very low agonist activity ($E_{max}$) that is less than about 10% of the $E_{max}$ of acetylcholine; (3) does not potently inhibit channel activations by an agonist if applied to a nAChR with the agonist simultaneously; and (4) potently inhibits channel activations by an agonist if the receptor is pre-incubated with the ligand for a period of time before the agonist is applied. Preferably, a nicotinic desensitizer is a ligand that has all of the above described characteristics. The term "ligand" as used herein refers to any organic chemical compound. Examples of the ligand include, but are not limited to a peptide, a protein, a nucleotide or its fragment, a polymer, and a natural or synthetic small molecule having a molecular weight of about 1,500 daltons or less.

The pharmacological profile of nicotinic desensitizers are markedly different from that of the classical nicotinic agonists. As used herein, the classical or typical nicotinic agonists refer to the conventional nicotinic agonists that are chemical substance capable of binding to a nAChR subtype to activate channel function of the receptor. The classical or typical nicotinic agonists include, but are not limited to acetylcholine and nicotine. The classical or typical nicotinic agonists are also known to have desensitizing effect on nAChRs. Thus the classical or typical nicotinic agonists have dual biological activity, i.e., activation and desensitization. In contrast, nicotinic desensitizers of the present invention are chemical substance capable of desensitizing a nAChR subtype without exerting substantial agonist activity. The term "chemical substance" can be any organic chemical compound. Examples of the chemical substance include, but are not limited to a peptide, a protein, a nucleotide or its fragment, a polymer, and a natural or synthetic small molecule having a molecular weight of about 1,500 daltons or less. As used herein, the term "substantial agonist activity" denotes a agonist activity ($E_{max}$) to a nAChR subtype that is less than about 10% of the $E_{max}$ of a typical nicotinic agonist to the nAChR subtype. It should be understood that the term "nicotinic agonists" as referred to in the present application include both nicotinic agonists and partial nicotinic agonists.

One of the examples of nicotinic desensitizer is sazetidine-A, which is one embodiment of compounds of formula (I). The characterization of in vitro pharmacological properties of sazetidine-A reveals that sazetidine-A has a novel pharmacological profile. This ligand has a very high equilibrium binding affinity for the $\alpha 4\beta 2$ nAChRs. However, in ion efflux assays, sazetidine-A does not stimulate $^{86}$Rb$^+$ efflux from stably transfected cells expressing defined $\alpha 4\beta 2$ nAChRs, nor does it inhibit nicotine stimulated $^{86}$Rb$^+$ efflux when it is applied simultaneously with nicotine. But sazetidine-A potently inhibits nicotine-stimulated $^{86}$Rb$^+$ efflux potently after cells are exposed to it for 10 min. It appears that sazetidine-A can desensitize the $\alpha 4\beta 2$ nAChRs without activating them. This unique profile distinguishes sazetidine-A from all known nicotinic agonist, competitive antagonists or noncompetitive antagonists. It has been proposed that sazetidine-A belongs to a new class of nicotinic ligands, i.e., nicotinic desensitizers. One of the important pharmacological characteristics of nicotinic desensitizers is desensitization of a nAChRs subtype without activating them in a significant manner. Sazetidine-A has been discussed in more detail in Xiao, et al., Mol Pharmacol 70, 1454-1460 (October, 2006), the content of which is herein incorporated by reference in its entirety.

Pharmacological studies suggests that (1) sazetidine-A has a very low affinity to receptors in the resting state, therefore, it does not increase the probability of a receptor to be in the resting state; (2) sazetidine-A has a very low affinity to receptors in the open state, therefore, it does not increase the probability of a receptor to be in the open state; and (3) sazetidine-A has a very high affinity to receptors in the desensitized state, therefore, it increases the probability of receptors to be in the resting state. For a population of receptors, the overall effect of sazetidine-A is to shift receptors from the resting state to the desensitized state. After a period of time, sazetidine-A can shift most of the receptors to the desensitized state and stabilize them in the state.

The discovery of sazetidine-A strongly supports the following over all hypotheses: (1) the dual actions of nicotinic agonists, activation and desensitization, can be physically separated; (2) many of nicotinic agonist's in vivo effects are mediated predominantly, or solely, by desensitization; and (3) the nicotinic desensitizers may produce many of nicotinic agonist's in vivo effects.

Nicotine and other nicotinic agonists affects many aspects of behavior including addiction, stimulation, arousal, locomotion, antinociception, memory, cognition, fear associated learning, neurodegeneration, anxiety, depression, food intake, etc. Many of these behavioral effects may prove to be mediated mainly by desensitization. Thus, nicotinic desensitizers can be useful therapeutic agents. It is a new strategy to develop nicotinic desensitizers as therapeutics, which is different from prior and current strategies, such as developing agonists (including partial agonists). A nicotinic desensitizer that is highly selective to one or more nAChR subtypes may provide a better pharmacological profile than an agonist (partial agonist) does. For example, sazetidine-A can potently desensitize α4β2 nAChRs but has little, if any, agonist activity at either α3β4 or α4β2 subtypes. Among potential advantages, sazetidine-A should not have similar side effects that tebanicline and varenicline showed in clinic, which are caused by the α3β4 agonist activity.

This invention is directed to nicotinic desensitizers and methods of selecting, testing and using them.

Method of Selecting Nicotinic Desensitizers in Receptor, Cell and Tissue Models

In one embodiment of the present application, the method of screening one or more compounds to identify one or more nicotinic desensitizers comprises identifying a compound as a nicotinic desensitizer if said compound (1) has binding affinity ($K_d$ or $K_i$) less than about 1,000 nM to a nAChR subtype; (2) has agonist activity ($E_{max}$) to the nAChR subtype less than about 10% of the $E_{max}$ of a typical nicotinic agonist to the nAChR subtype; and (3) has potency of inhibiting receptor activation of the nAChR subtype by the typical agonist ($IC_{50(A)}$) more than about 1,000 nM when the compound is applied to the nAChR subtype simultaneously with the typical nicotinic agonist. Preferably, the method further comprising the following steps in any sequence: determining the binding affinity ($K_d$ or $K_i$) of each of the one or more compounds to a nAChR subtype; determining the agonist activity ($E_{max}$) of each of the one or more compounds to the nAChR subtype; and determining the antagonist activity of each of the one or more compounds to the nAChR subtype ($IC_{50(A)}$) by measuring the activation of channel function of a receptor of the nAChR subtype when each of the one or more compounds is applied to the nAChR subtype simultaneously with a typical nicotinic agonist.

In another embodiment, the present invention provides a method of screening one or more compounds to identify one or more nicotinic desensitizers. The method comprises identifying a compound as a nicotinic desensitizer if said compound (1) has agonist activity ($E_{max}$) to a nAChR subtype less than 10% of the $E_{max}$, of a typical nicotinic agonist to the nAChR subtype; (2) has potency of inhibiting receptor activation of the nAChR subtype by the typical nicotinic agonist via desensitization ($IC_{50(D)}$) less than about 10,000 nM; (3) has inhibition of receptor activation of the nAChR subtype by a typical nicotinic agonist ($IC_{50(A)}$) more than 1,000 nM when the compound is applied to the nAChR subtype simultaneously with the typical nicotinic agonist; and (4) the $IC_{50(D)}$<the $IC_{50(A)}$. The desensitization comprises contacting each of the one or more compounds with the nAChR subtype for a period of time before a typical nicotinic agonist is applied to the nAChR subtype. Preferably, the method further comprising the following steps in any sequence: determining the agonist activity ($E_{max}$) of said one or more compounds to the nAChR subtype; determining the desensitization activity of said one or more compounds to the nAChR subtype ($IC_{50(D)}$) by measuring the activation of channel function of a receptor of the nAChR subtype after the desensitization; and determining the antagonist activity of said one or more compounds to the nAChR subtype ($IC_{50(A)}$) by measuring the activation of channel function of the receptor of the nAChR subtype when each of the one or more compounds is applied to the nAChR subtype simultaneously with the typical nicotinic agonist.

In one embodiment of the present invention, the $K_d$ or $K_i$ is less than about 750 nM. In another embodiment of the present invention, the $K_d$ or $K_i$ is less than about 500 nM. In another embodiment of the present invention, the $K_d$ or $K_i$ is less than about 250 nM. In another embodiment of the present invention, the $K_d$ or $K_i$ is less than about 100 nM. In one embodiment of the present invention, the $E_{max}$ of the compound is less than about 9% of the $E_{max}$ of a typical nicotinic agonist. In another embodiment of the present invention, the $E_{max}$ of the compound is less than about 8% of the $E_{max}$ of a typical nicotinic agonist. In another embodiment of the present invention, the $E_{max}$ of the compound is less than about 7% of the $E_{max}$ of a typical nicotinic agonist. In another embodiment of the present invention, the $E_{max}$ of the compound is less than about 6% of the $E_{max}$ of a typical nicotinic agonist. In another embodiment of the present invention, the $E_{max}$ of the compound is less than about 5% of the $E_{max}$ of a typical nicotinic agonist. In one embodiment of the present invention, the $IC_{50(A)}$ is more than about 2,500 nM. In another embodiment of the present invention, the $IC_{50(A)}$ is more than about 5,000 nM. In another embodiment of the present invention, the $IC_{50(A)}$ is more than about 10,000 nM. In one embodiment of the present invention, the $IC_{50(D)}$ is less than about 5,000 nM. In another embodiment of the present invention, the $IC_{50(D)}$ is less than about 2,500 nM. In another embodiment of the present invention, the $IC_{50(D)}$ is less than about 1,000 nM.

In the present invention, the typical nicotinic agonists include, but are not limited to acetylcholine and nicotine. The period of time for desensitization may be about 1 second to about 2 hours. The period of time for desensitization may be about 10 seconds, 30 seconds, 1 minute, 5 minutes, 10 minutes, 20 minutes, 30 minutes, 40 minutes, 50 minutes, 1 hour, 1.5 hours, or 2 hours; or any period of time therebetween.

The method of the present invention allows the screening of a compound in receptor and cell models to determine whether the compound is a nicotinic desensitizer. For the purpose of selecting or screening one or more compounds to identify one or more nicotinic desensitizers, the terms "compound" and "test compound" are used interchangeably. In yet anther embodiment, the method of the present invention comprises the following aspects without preference to the sequences thereof:

(a) a nicotinic desensitizer has high affinity for desensitized state of one or more targeted receptor subtypes. The binding affinity can be determined by in vitro equilibrium ligand binding assays, in which the test compound is incubated with receptors, in the presence or absence of other known nicotinic ligands, for a certain period of time (seconds, minutes, or hours) before occupancy of receptor binding sites are measured. The binding affinity can also be determined by in vitro kinetic binding assays. The binding affinity can be expressed as the equilibrium dissociation constant ($K_d$ or $K_i$), % of occupancy, ratio of dissociation rate constant and association rate constant ($k_{off}/k_{on}$), etc;

(b) a nicotinic desensitizer has very low affinity, if any, for the open state of receptors. Therefore, it does not have significant agonist activity at receptors. The agonist activity can be determine by in vitro stimulation (activation) assays, in which different concentrations of the test compound are applied to receptors and the activation of channel function of receptors are measured. If there is any agonist activity is observed, the relative efficacy of the test compound can be obtained by comparing the maximal stimulation, $E_{max}$, of the test compound to $E_{max}$ of a typical nicotinic agonist, such as acetylcholine or nicotine;

(c) a nicotinic desensitizer may have some affinity for the resting state of receptors. Therefore, when it is applied simultaneously with a nicotinic agonist, it may antagonize the agonist activated receptor channel function. The potency of the antagonist activity can be determine by in vitro antagonism assays, in which different concentrations of the test compound are applied to receptors simultaneously with a concentration of an agonist and the activation of channel function of receptors are measured. The potency of this classical antagonist activity can be expressed as acute inhibition concentration 50% ($IC_{50(A)}$);

(d) a nicotinic desensitizer must be able to desensitize receptors. The potency of desensitizing receptors can be determine by in vitro desensitization assays, in which different concentrations of the test compound are applied to receptors alone for a period of time (seconds, minutes or hours) before a typical nicotinic agonist, such as acetylcholine or nicotine, with or without the test compound, is applied and the channel function is determined. The potency of this inhibition via desensitization can be expressed as desensitizing inhibition concentration 50% ($IC_{50(D)}$);

(e) a nicotinic desensitizer can be identified if a test compound (1) has high binding affinity to a nAChR subtype ($K_d$ or $K_i$ less than 1,000 nM); (2) does not have significant agonist activity at the subtype ($E_{max}$ less than 10% of $E_{max}$ of a typical nicotinic agonist of this subtype, such as acetylcholine or nicotine); and (3) does not have strong inhibition of the receptor activation by a typical agonist if the compound is applied simultaneously with the agonist ($IC_{50(A)}$) more than 1,000 nM); and alternatively, (f) a nicotinic desensitizer can also be identified if a test compound (1) does not have significant agonist activity at a subtype ($E_{max}$ less than 10% of $E_{max}$ of a typical nicotinic agonist of this subtype, such as acetylcholine or nicotine); and (2) has a high potency of inhibiting receptor activation by an agonist via desensitization ($IC_{50(D)}$) less than 10,000 nM at any pre-treating time period); (3) does not have strong inhibition of the receptor activation by a typical agonist if the compound is applied simultaneously with the agonist ($IC_{50(A)}$ more than 1,000 nM); and (4) the $IC_{50(D)}$<the $IC_{50(A)}$.

It should be understood that the characterization of sazetidine-A as a selective α4β2 nAChR desensitizer as described below is offered to further illustrate the methods of selecting nicotinic desensitizers, not to limit the scope thereof.

Binding Affinities of Sazetidine-A at nAChR Subtypes

Binding of [$^3$H]EB to nAChRs was measured as described previously (Xiao et al., 1998). Briefly, cultured cells at >80% confluence were removed from their flasks (80 cm$^2$) with a disposable cell scraper and placed in 10 ml of 50 mM Tris HCl buffer (pH 7.4, 4° C.). The cell suspension was centrifuged at 10,000×g for 5 min and the pellet was collected. For cells treated chronically with nicotinic agonists during culturing, the pellet was washed two more times by centrifugation in fresh buffer to remove residual drug. The cell pellet was then homogenized in 10 ml buffer with a polytron homogenizer (Model PT2100, 12 mm aggregate, 26,000 rpm, 20 seconds) and centrifuged at 36,000 g for 10 min at 4° C. The membrane pellet was resuspended in fresh buffer, and aliquots of the membrane preparation equivalent to 30 to 200 μg protein were used for binding assays. The concentration of [$^3$H]EB used was ~100 pM for competition binding assays, and approximately ~2.4 nM, which is close to a saturation concentration for the α4β2 receptor subtype, for measuring receptor density. Nonspecific binding was assessed in parallel incubations in the presence of 300 μM nicotine. Bound and free ligands were separated by vacuum filtration through Whatman GF/C filters treated with 0.5% polyethylenimine. The filter-retained radioactivity was measured by liquid scintillation counting. Specific binding was defined as the difference between total binding and nonspecific binding. Data from saturation and competition binding assays were analyzed using Prism 4 (GraphPad Software, San Diego, Calif.). Additional statistical analyses are indicated in the figure legends.

All ligand binding assays were carried out using rat or human nAChRs heterologously expressed in human cells or in native rat brain tissues. As shown in FIG. 1 and summarized in Table 1, sazetidine-A competes with very high affinity for rat and human α4β2nAChRs heterologously expressed in cells or from rat brain; moreover, its binding affinity for the heterologously expressed rat α4β2 receptors is 24,000 times higher than for rat α3β4 receptors. As shown in Table 1, the selectivity of sazetidine-A for α4β2 receptors over α3β4 receptors ($K_i$ ratio) was much greater than that of nicotine or dihydro-β-erythroidine (DHβE), both of which are relatively selective ligands for α4β2 nAChRs in binding assays (Xiao and Kellar, 2004). The affinity of sazetidine-A for heterologously expressed rat and human α4β2 subtype is comparable to its affinity for native nAChRs from rat forebrain, which expresses predominantly the α4β2 subtype (Flores et al., 1992; Whiting and Lindstrom, 1987).

TABLE 1

Comparison of binding affinities of Sazetidine-A, nicotine and DHβE at nAChR subtypes.

| | $K_i$ (nM) | | | | Selectivity |
|---|---|---|---|---|---|
| Ligand | α4β2 (rat) | α4β2 (human) | Forebrain (rat) | α3β4 (rat) | ($K_i$ ratio: rat α3β4/rat α4β2) |
| Sazetidine-A | 0.41 ± 0.16 | 0.64 ± 0.32 | 0.94 ± 0.48 | 10,000 ± 3 000 | 24,000 |
| (−)-Nicotine | 10 ± 2 | 8.2 ± 0.2 | 12 ± 2 | 440 ± 60 | 44 |
| DHβE | 600 ± 70 | 410 ± 30 | 130 ± 50 | 110,000 ± 10,000 | 180 |

Binding was measured using 100 pM [$^3$H]EB as described in Methods. Values are the mean ± SEM of 3 to 5 independent experiments. The $K_i$ values of nicotine and DHβE at rat nAChRs were published previously (Xiao and Kellar, 2004) and are shown here for comparison. Approximately 90% of the nAChRs in rat forebrain are the α4β2 subtype.

$^{86}Rb^+$ Efflux Assays

Functional properties of compounds at nAChRs expressed in the transfected cells were measured using $^{86}R^+$ efflux assays as described previously (Xiao et al., 1998). In brief, cells were plated into 24-well plates coated with poly-D-lysine. The plated cells were grown at 37° C. for 18 to 24 hour to reach 85-95% confluence. The cells were then incubated in growth medium (0.5 ml/well) containing $^{86}Rb^+$ (2 µCi/ml) for 4 hour at 37° C. The loading mixture was then aspirated, and the cells were washed four times with 1 ml buffer (15 mM HEPES, 140 mM NaCl, 2 mM KCl, 1 mM $MgSO_4$, 1.8 mM $CaCl_2$, 11 mM Glucose, pH 7.4). One ml of buffer with or without compounds to be tested was then added to each well. After incubation for 2 min, the assay buffer was collected for measurements of $^{86}Rb^+$ released from the cells. Cells were then lysed by adding 1 ml of 100 mM NaOH to each well, and the lysate was collected for determination of the amount of $^{86}Rb^+$ that was in the cells at the end of the efflux assay. Radioactivity of assay samples and lysates was measured by liquid scintillation counting. Total loading (cpm) was calculated as the sum of the assay sample and the lysate of each well. The amount of $^{86}Rb^+$ efflux was expressed as a percentage of $^{88}Rb^+$ loaded. Stimulated $^{86}Rb^+$ efflux was defined as the difference between efflux in the presence and absence of nicotine. For obtaining an $IC_{50}$ value, inhibition curves were constructed in which different concentrations of an antagonist were included in the assay to inhibit efflux stimulated by 100 µM nicotine. $IC_{50}$ values were determined by nonlinear least-squares regression analyses (GraphPad, San Diego, Calif.).

Agonist Activity of Sazetidine-A at nAChR Subtypes

Figure 2A:
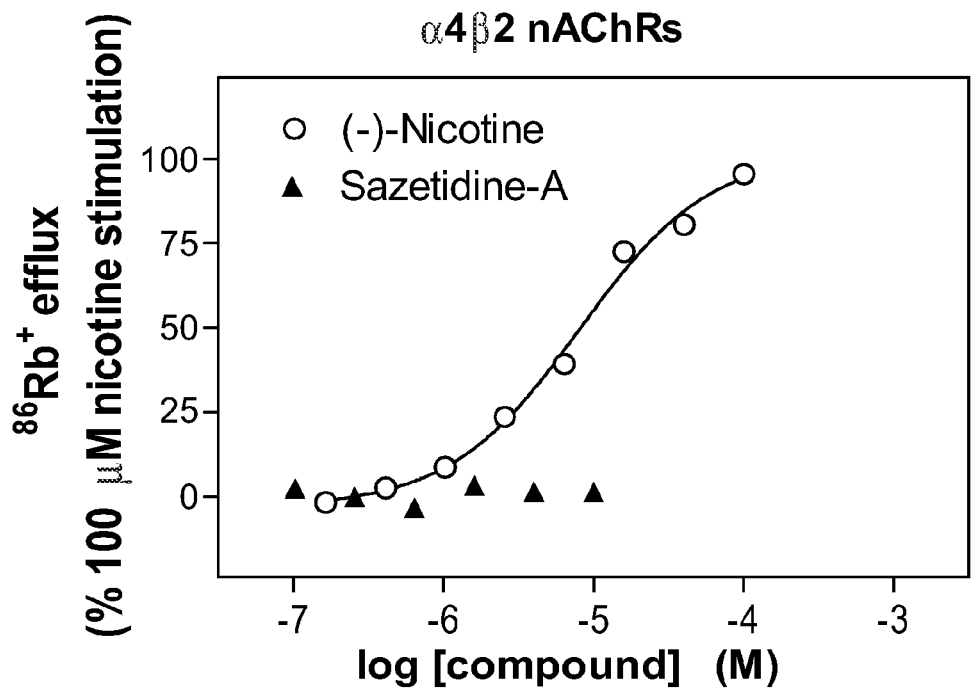
FIGS. 2A and 2B. Comparison of agonist activity of sazetidine-A and nicotine. The agonist activity of sazetidine-A and nicotine at nAChRs was compared by measuring the stimulation of $^{86}$Rb$^+$ efflux by each compound in cells expressing human $\alpha 4\beta 2$ and rat $\alpha 3\beta 4$ nAChRs, as described in Methods. Data shown are representative of 4 to 7 independent experiments. The EC$_{50}$ values (mean±SEM) for nicotine activation of channel function were 10±1 µM at the human $\alpha 4\beta 2$ receptors (FIG. 2A) and 34±5 µM at the rat $\alpha 3\beta 4$ receptors (FIG. 2B). EC$_{50}$ values for sazetidine-A could not be calculated.
Figure 2B:
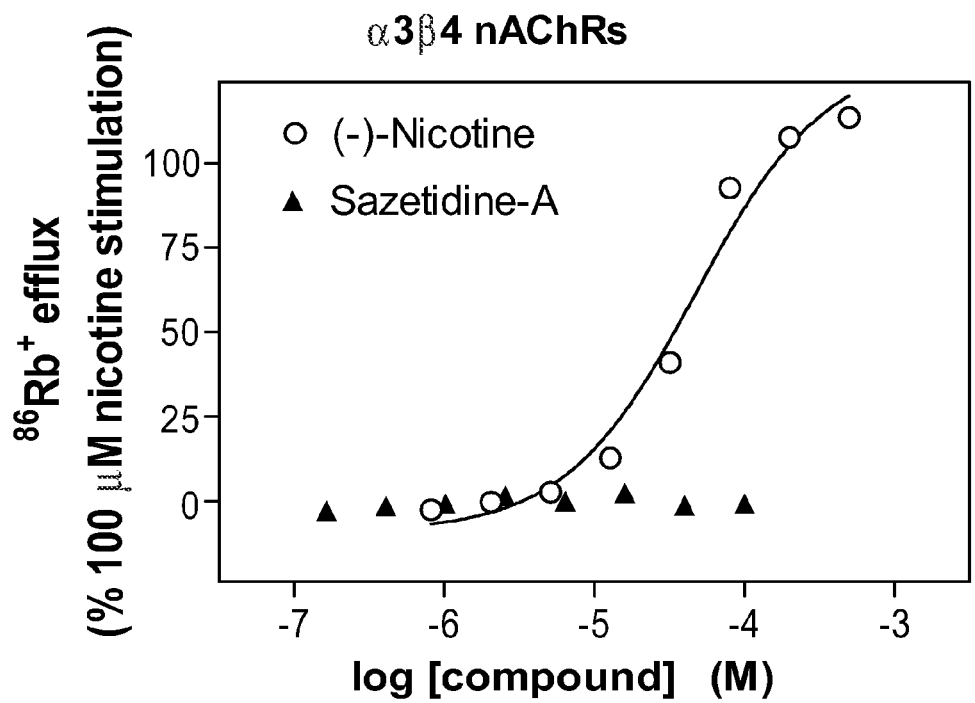

The agonist activities of ligands on nAChRs were assessed by measuring agonist-stimulated $^{86}Rb^+$ efflux from stably transfected cells. Consistent with previous reports, nicotine stimulates $^{86}Rb^+$ release mediated by both α4β2 (Eaton et al., 2003) and α3β4 (Xiao et al., 1998) nAChR subtypes in a concentration dependent manner (FIGS. 2A and 2B). In contrast, sazetidine-A showed no agonist activity at either nAChR subtype over a wide concentration range (FIGS. 2A and 2B). This indicates that sazetidine-A does not activate nAChR channel function, or its action is so weak and/or the duration of its action is so transient, that no measurable channel function can be detected by the $^{86}Rb^+$ efflux method.

Acute Antagonist Activity of Sazetidine-A at nAChR Subtypes

Figure 3A:
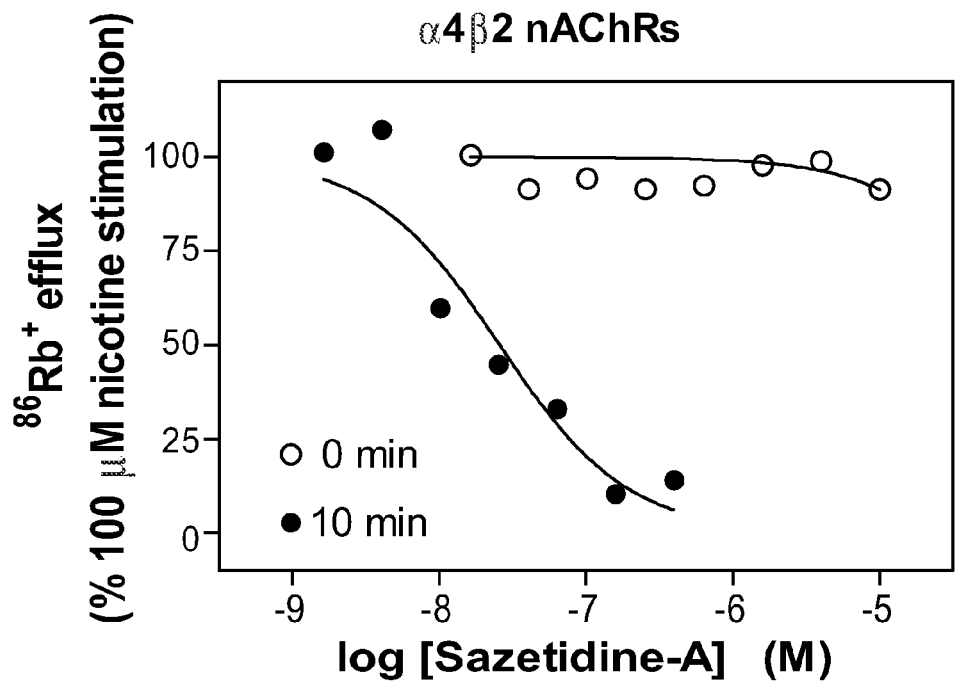
FIG. 3. Comparison of inhibitory effects of sazetidine-A on nAChR channel function with or without a 10 min pretreatment. The $^{86}$Rb$^+$ efflux assays in cells expressing human $\alpha 4\beta 2$ (FIG. 3A) and rat $\alpha 3\beta 4$ (FIG. 3B) nAChRs were carried out as described In Methods. Cells were either preincubated with buffer alone and then exposed simultaneously to 100 µM nicotine and the indicated concentration of sazetidine-A (0 min, no pretreatment group), or the cells were preincubated for 10 min with the indicated concentration of sazetidine-A alone and then exposed to 100 µM nicotine plus sazetidine-A (10 min, pretreatment group). Concentration-effect curves are representative of 3-7 independent experiments. See Table 2 for a summary of IC$_{60}$ values for sazetidine-A from all experiments.
Figure 3B:
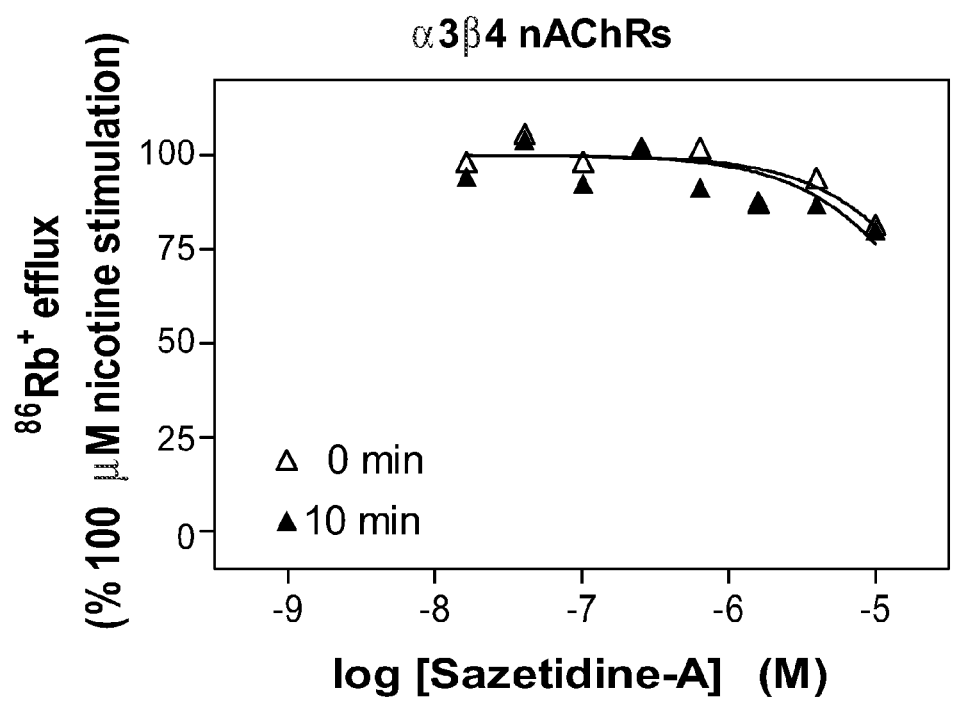

The acute antagonist activity of sazetidine-A was evaluated by measuring its blockade of nicotine-stimulated $^{86}Rb^+$ efflux. When sazetidine-A was added simultaneously with nicotine no antagonist activity in cells expressing either α4β2 or α3β4 nAChRs was detected (FIGS. 3A and 3B, and Table 2).

Desensitization Activity of Sazetidine-A at nAChR Subtypes

When preincubated with the cells for 10 min, sazetidine-A potently inhibited nicotine activation of the α4β2 receptors with an $IC_{50}$ value of ~30 nM, and it nearly completely inhibited activation at ~200 nM. In contrast, even with the 10 min preincubation, sazetidine-A was still ineffective in blocking α3β4 nAChRs (FIGS. 3A and 3B, and Table 2).

Sazetidine-A is an α4β2 nAChR Desensitizer

The potency of sazetidine-A in desensitizing α4β2 nAChRs ($IC_{50(D,10\ min)}$=26 nM) is much higher than the potency of sazetidine-A in acutely antagonizing the receptors ($IC_{50(A)}$>=10,000 nM). It is very obvious that sazetidine-A is an α4β2 nAChR desensitizer.

For comparison, we also examined three other nicotinic ligands in the same manner. DHβE, a relatively potent and selective competitive antagonist of α4β2 nAChRs, blocked nicotine activation of the α4β2 subtype with an $IC_{50}$ value of ~1.4 µM (Table 2). In contrast to sazetidine-A, however, the potency of DHβE was similar with or without the 10 min preincubation. DHβE also blocked nicotine activation of the α3β4 subtype but with ~100-fold lower potency than it did the α4β2 subtype (Table 2).

TABLE 2

Inhibition of nAChR function by sazetidine-A, DHβE, varenicline and nicotine. nAChR function in cells expressing human α4β2 nAChRs and rat α3β4 nAChR was measured in the nicotine-stimulated $^{86}Rb^+$ efflux assays, as described above.
The $IC_{50}$ values were derived from inhibition curves as shown in FIG. 3 and are the mean ± SEM of 3 to 7 independent experiments.

| | $IC_{50}$ (nM) | |
|---|---|---|
| Compound | α4β2 nAChRs | α3β4 nAChRs |
| Sazetidine-A | | |
| 0 min Pretreatment | >10,000 | >10,000 |
| 10 min Pretreatment | 26 ± 7 | >10,000 |
| DHβE | | |
| 0 min Pretreatment | 1,400 ± 200 | 160,000 ± 20,000 |
| 10 min Pretreatment | 1,400 ± 300 | 130,000 ± 58,000 |

In one embodiment of the present invention, the nicotinic desensitizers are compounds of formula (I):

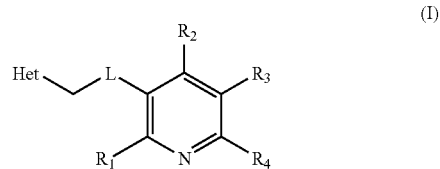

or a pharmaceutically acceptable tautomer, salt, solvate, and/or ester thereof, wherein, L is O, S, or $NR^5$; Het is heterocyclyl; each $R^1$, $R^2$, $R^3$, and $R^4$, is independently H, halo, amino, N-alkyl amino, N,N-dialkyl amino, amido, nitro, cyano, hydroxyl, alkoxy, or an optionally substituted $C_1$-$C_{12}$ alkyl, $C_2$-$C_{12}$ alkenyl, or $C_2$-$C_{12}$ alkynyl, wherein the substituents are selected from the group consisting of hydroxyl, halo, amino, N-alkyl amino, N,N-dialkyl amino, —NH—C(O)—$R^6$, —NH—C(O)—$OR^6$, —O—C(O)—$R^6$, —O—C(O)—$OR^6$, nitro, and alkoxy; $R^5$ is H, or an optionally $C_1$-$C_6$ alkyl, $C_2$-$C_6$ alkenyl, or $C_2$-$C_6$ alkynyl; and $R^6$ is an optionally substituted $C_1$-$C_6$ alkyl, $C_2$-$C_6$ alkenyl, $C_2$-$C_6$ alkynyl, aryl, or heteroaryl.

In one preferred embodiment of the compound of formula (I), each $R^1$, $R^2$, and $R^4$ is independently H, halo, amino, N-alkyl amino, N,N-dialkyl amino, amido, nitro, cyano, hydroxyl, or alkoxy. In another preferred embodiment of the compound of formula (I), $R^3$ is an optionally substituted $C_1$-$C_{12}$ alkyl, $C_2$-$C_{12}$ alkenyl, or $C_2$-$C_{12}$ alkynyl. In yet another preferred embodiment of the compound of formula (I), Het is a 4- to 7-membered monocyclic fully-saturated heterocyclic ring containing at least one hetero atom selected from the group consisting of N, O, and S. In one more preferred embodiment of the compound of formula (I), each $R^1$, $R^2$, and $R^4$ is H; $R^3$ is an optionally substituted $C_1$-$C_{12}$ alkyl, $C_2$-$C_{12}$ alkenyl, or $C_2$-$C_{12}$ alkynyl; and Het is a 4- to 7-membered monocyclic fully-saturated heterocyclic ring containing at least one hetero atom selected from the group consisting of N, O, and S.

In another embodiment of the present invention, the nicotinic desensitizers are compounds of formula (II):

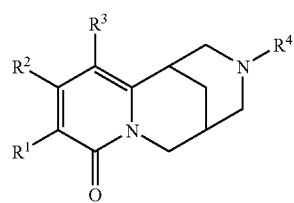

(II)

or a pharmaceutically acceptable tautomer, salt, solvate, and/or ester thereof, wherein, $R^1$, $R^2$, and $R^3$ are each independently H, halo, amino, N-alkyl amino, N,N-dialkyl amino, amido, nitro, cyano, hydroxyl, alkoxy, or an optionally substituted $C_1$-$C_6$ alkyl, $C_2$-$C_8$ alkenyl, or $C_2$-$C_6$ alkynyl, wherein the substituents are selected from the group consisting of hydroxyl, halo, amino, nitro, and alkoxy; and $R^5$ is H, an optionally substituted $C_1$-$C_6$ alkyl, $C_2$-$C_6$ alkenyl, or $C_2$-$C_{10}$ alkynyl; wherein the substituents are selected from the group consisting of hydroxyl, halo, amino, nitro, and alkoxy.

In one preferred embodiment of the compound of formula (II), $R^4$ is H. In another preferred embodiment of the compound of formula (II), $R^3$ are H. In one more preferred embodiment of the compound of formula (II), $R^3$ and $R^4$ are H.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). "Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). "Alkenyl" is a hydrocarbon containing normal, secondary, tertiary or cyclic carbon atoms with at least one site of unsaturation, i.e. a carbon-carbon, $sp^2$ double bond. "Alkynyl" is a hydrocarbon containing normal, secondary, tertiary or cyclic carbon atoms with at least one site of unsaturation, i.e. a carbon-carbon, sp triple bond.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like. "Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

The term "substituted" in reference to alkyl, alkylene, aryl, heteroaryl, etc., for example, "substituted alkyl", "substituted alkylene", "substituted aryl", and "substituted heteroaryl", means alkyl, alkylene, aryl, heteroaryl, respectively, in which one or more hydrogen atoms are each independently replaced with a non-hydrogen substituent. Typical substituents include, but are not limited to, —X, —R, —O⁻, =O, —OR, —SR, —S⁻, —NR₂, —N⁺R₃, =NR, —CX₃, —CN, —OCN, —SCN, —N=C=O, —NCS, —NO, —NO₂, =N₂, —N₃, —NHC(=O)R, —C(=O)R, —C(=O)NRR—S(=O)₂O⁻, —S(=O)₂OH, —S(=O)₂R, —OS(=O)₂OR, —S(=O)₂NR, —S(=O)R, —OP(=O)(OR)₂, —N(=O)(OR)₂, —N(=O)(O⁻)₂, —N(=O)(OH)₂, —N(O)(OR)(O⁻), —C(=O)R, —C(=O)X, —C(S)R, —C(O)OR, —C(O)O⁻, —C(S)OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted. "Optionally substituted" refers to a particular moiety of the compound of Formula (I) (e.g., an optionally substituted aryl group) refers to a moiety having 0, 1, 2, or more substituents.

In one embodiment of the present invention, a compound of formula (I) is selected from a group consisting of

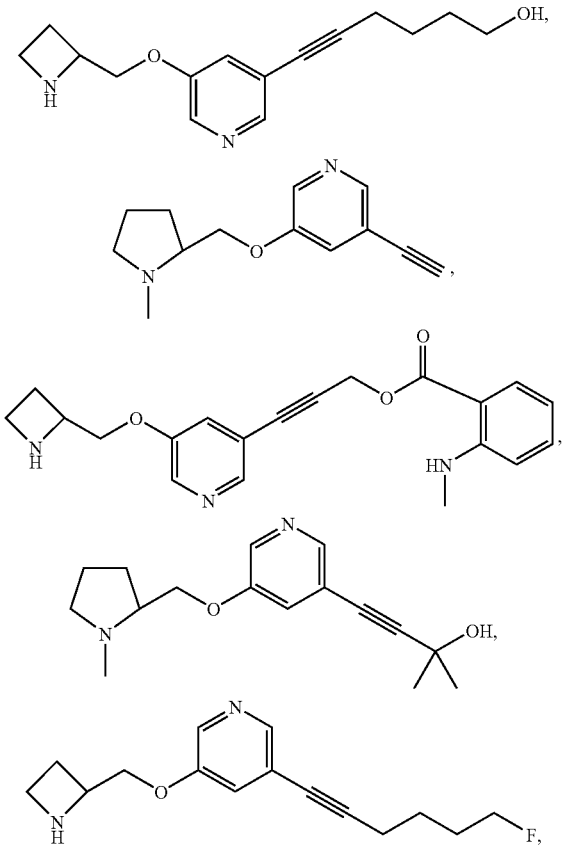

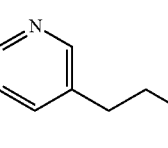

or a pharmaceutically acceptable tautomer, salt, solvate, and/or ester thereof.

In one embodiment of the present invention, a compound of formula (II) is selected from a group consisting of

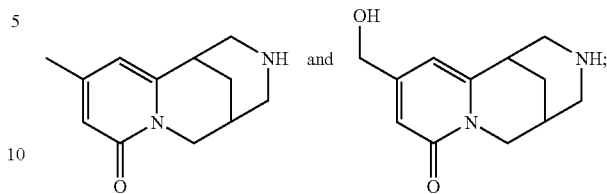

or a pharmaceutically acceptable tautomer, salt, solvate, and/or ester thereof.

Methods of Testing Nicotinic Desensitizers in Animal Models

Laboratory animal models have been used for studying behavioral effects of nicotine and nicotinic ligands for many years. There are many animal disease models available for testing the therapeutic effects of therapeutic agents. All these animal models can be used to test nicotinic desensitizers that are selected by the methods of the present invention. In one embodiment, the present invention provides a method of testing one or more desensitizers in an animal behavior or disease model. The method comprises administering one or more desensitizers to an animal which belongs to one certain animal model; and evaluating the physiological and behavioral changes in said animal to determine whether the one or more desensitizers have certain in vivo effects. For example, rodent drug discrimination model, conditioned place preference model and self administration model can be used to test effects of a desensitizer related to nicotine addiction and to test the potential usage of it as a smoking cessation drug. For another example, rodent acute thermal pain model (tail-flick), mechanical pain model (paw-pressure), chemical pain model (para-phenylquinone), persistent pain model (Formalin), chronic pain model (arthritis) and neuropathic pain model (nerve ligation) can be used to evaluate the possibility of a desensitizer as a new analgesic drug.

Use of Nicotinic Desensitizers as Therapeutic Agents

In one embodiment, the present invention provides a pharmaceutical composition comprising a therapeutically effective amount of at least one nicotinic desensitizer, or a pharmaceutically acceptable salt, solvate, and/or ester thereof; and a pharmaceutically acceptable carrier or excipient. In another embodiment of the present invention, the pharmaceutical composition further comprises at least one active agent.

"Ester thereof" means any ester of a nicotinic desensitizer in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The term "ester thereof" includes but is not limited to pharmaceutically acceptable esters thereof.

"Salt thereof" means any acid and/or base addition salt of a nicotinic desensitizer according to the invention; preferably a pharmaceutically acceptable salt thereof.

"Solvate thereof" means a nicotinic desensitizer formed by solvation (the combination of solvent molecules with molecules or ions of the solute), or an aggregate that consists of a solute ion or molecule (the nicotinic desensitizer) with one or more solvent molecules.

"Pharmaceutically acceptable salt" means a salt of a nicotinic desensitizer which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the nicotinic desensitizer, the term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

"Treatment" or "treating" means the administration of a nicotinic desensitizer or composition according to the present invention to alleviate or eliminate symptoms of one or more conditions or diseases as described herein in a patient.

It should be understood that the term "nicotinic desensitizer" as used herein includes all tautomers, stereoisomers, diastereomer, and enantiomers of a nicotinic desensitizer having a particular chemical structure.

"Chiral" refers to molecules which have the property of non-superimposability of the mirror image partner, while the term "achiral" refers to molecules which are superimposable on their mirror image partner.

"Tautomers" refer to isomers of nicotinic desensitizers in which the isomers change into one another with great ease so that they ordinarily exist together in equilibrium.

"Stereoisomers" refer to nicotinic desensitizers which have identical chemical constitution, but differ with regard to the arrangement of the atoms or groups in space.

"Diastereomer" refer to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a nicotinic desensitizer which are non-superimposable mirror images of one another.

Stereochemical definitions and conventions used herein generally follow S. N. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The nicotinic desensitizers of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients, such as the at least one nicotinic desensitizer, to be administered alone it may be preferable to present them as pharmaceutical formulations. The formulations of the invention, both for veterinary and for human use, comprise at least one active ingredient, as defined above, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more nicotinic desensitizers of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl n-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 µm (including particle sizes in a range between 0.1 and 500 µm in increments such as 0.5 µm, 1 µm, 30 µm, 35 µm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Nicotinic desensitizers of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

Another embodiment of the present invention is directed to the use of nicotinic desensitizers for the treatment of diseases and conditions associated with aging, addiction, pain, obesity, schizophrenia, epilepsy, mania and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, amyotrophic lateral sclerosis, inflammation, stoke, spinal-cord injury, and etc. It should be understood that the use includes compounds comprising either a desensitizer as the only active substance, or a desensitizer in combination with one or more other therapeutic agents.

Administering a therapeutically effective amount of a nicotinic desensitizer to patients may lead to changes of nAChRs and their functional status, which have therapeutically beneficial effects to patients.

In one embodiment, the present invention provides a method for treating, preventing, or reversing one or more conditions or diseases in a patient suffering said one or more conditions comprising administering to the patient a therapeutically effective amount of at least one nicotinic desensitizer, or pharmaceutically acceptable salt, solvate, and/or ester thereof. Examples of the conditions or diseases include, but are not limited to aging, addiction, pain, obesity, schizophrenia, epilepsy, mania and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, amyotrophic lateral sclerosis, inflammation, stoke, and spinal-cord injury. In another embodiment, the method further comprises co-administering at least one additional active agent. The co-administering may be simultaneous or sequential. Preferably, the patient is a mammal. More preferably, the patient is a human.

One or more nicotinic desensitizers of this invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient.

As used herein, the term "therapeutically effective amount" means an amount that is effective to exhibit therapeutic or biological activity at the site(s) of activity in a mammalian subject, without undue adverse side effects (such as undue toxicity, irritation or allergic response), commensurate with a reasonable benefit/risk ratio when used in the manner of the present invention. By "pharmaceutically acceptable", it is meant being compatible with the other ingredients of the formulation and physiologically innocuous to the recipient thereof. The at least one active agent can be any compound having therapeutic effect. One example of the at least one active agent is varenicline. It is also possible to combine any nicotinic desensitizers of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

In one embodiment, the at least one nicotinic desensitizer is a compound (1) the binding affinity ($K_d$ or $K_i$) of which to a nAChR subtype is less than about 1,000 nM; (2) the agonist activity ($E_{max}$) of which for the nAChR subtype is less than about 10% of the $E_{max}$ of a typical nicotinic agonist for the nAChR subtype; and (3) the inhibition of which to receptor activation of the nAChR subtype by the typical nicotinic agonist ($IC_{50(A)}$) is more than about 1,000 nM when the compound is applied to the nAChR subtype simultaneously with the typical agonist.

In another embodiment, the at least one nicotinic desensitizer is a compound (1) the agonist activity ($E_{max}$) of which for a nAChR subtype is less than about 10% of the $E_{max}$ of a typical nicotinic agonist for the nAChR subtype; (2) the inhibition of which to receptor activation of the nAChR subtype by the typical nicotinic agonist via desensitization ($IC_{50(D)}$) is less than about 10,000 nM; (3) the inhibition of which to receptor activation of the nAChR subtype by a typical nicotinic agonist ($IC_{50(A)}$) is more than about 1,000 nM when the compound is applied to the nAChR subtype simultaneously with the typical agonist; and (4) the $IC_{50(D)} <$ the $IC_{50(A)}$; wherein the desensitization comprises contacting the compound with the nAChR subtype for a period of time before the typical nicotinic agonist is applied to the nAChR subtype.

In yet another embodiment, the at least one nicotinic desensitizer is a compound of formula (I) or (II).

The therapeutic effective amount of a nicotinic desensitizer of the present invention varies not only with the particular compound selected, but also with the route of administration, the nature of the condition for which treatment is required, and the age and condition of the patient. It would be appreciated by one skilled in the art that the therapeutic effective amount of a nicotinic desensitizer of the present invention is ultimately at the discretion of the attendant physician or veterinarian. In general, however, a suitable dose will range from about 0.01 to about 750 mg/kg of body weight per day, preferably in the range of 0.5 to 60 mg/kg/day, most preferably in the range of 1 to 20 mg/kg/day for systemic administration, or for topical applications a suitable dose will range from about 0.001 to 25% wt/vol, preferably in the range of 0.001 to 5% wt/vol of formulated material. If the material is to be microdispersed (micronized) instead of molecularly dispersed in solution, and applied thus, then the effective amount of the dose could range from 0.01 to 25 weight percent of micronized nicotinic desensitizer.

In one embodiment, the present invention provides a new pharmaceutical composition or use for the preparation of a medicament, substantially as described herein. In another embodiment, the present invention provides a nicotinic desensitizer as a therapeutic substance. For example, the present invention provides the use of a nicotinic desensitizer for the manufacture of a medicament for the treatment of one or more conditions or diseases associated with aging, addiction, pain, obesity, schizophrenia, epilepsy, mania and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, amyotrophic lateral sclerosis, inflammation, stoke and spinal-cord injury. For another example, the present invention provides the use of a nicotinic desensitizer for the preparation of a medicament for the treatment of one or more conditions or diseases associated with aging, addiction, pain, obesity, schizophrenia, epilepsy, mania and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, amyotrophic lateral sclerosis, inflammation, stoke and spinal-cord injury. In one embodiment of the uses as described above, the medicament further comprises at least one additional active agent.

EXAMPLES

The present invention is further explained by the following examples of nicotinic desensitizers that are intended to be for illustrative and non-limiting purpose.

Example 1

Sazetidine-A

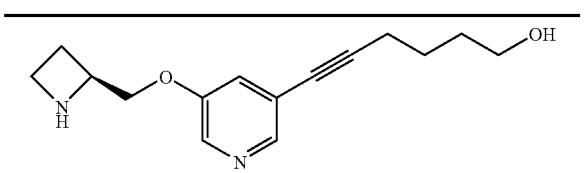

6-[5-(Azetidin-2-ylmethoxy)-pyridin-3-yl]-hex-5-yn-1-ol

| Property | nAChR Subtype | |
|---|---|---|
| | α4β2 | α3β4 |
| Equilibrium binding affinity ($K_i$, nM) | 0.41 | 10,000 |
| Agonist Activity | Not detected | Not detected |
| Acute Antagonist Potency ($IC_{50(A)}$, nM) | >10,000 | >10,000 |
| Desensitization Potency ($IC_{50(D,10\ min)}$, nM) | 26 | >10,000 |

Example 2

Sazetidine-B

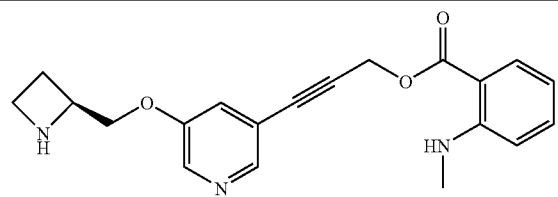

2-Methylamino-benzoic acid 3-[5-(azetidin-2-ylmethoxy)-pyridin-3-yl]-prop-2-ynyl ester

| Property | nAChR Subtype | |
|---|---|---|
| | α4β2 | α3β4 |
| Equilibrium binding affinity ($K_i$, nM) | 0.22 | 1300 |
| Agonist Activity | Not detected | Not detected |
| Acute Antagonist Potency ($IC_{50(A)}$, nM) | >10,000 | >10,000 |
| Desensitization Potency ($IC_{50(D,10\,min)}$, nM) | 30 | 6,000 |

Example 3

ZW-104

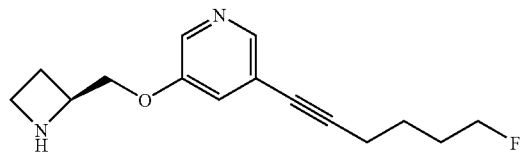

3-(Azetidin-2-ylmethoxy)-5-(6-fluoro-hex-1-ynyl)-pyridine

| Property | nAChR Subtype | |
|---|---|---|
| | α4β2 | α3β4 |
| Equilibrium binding affinity ($K_i$, nM) | 0.21 | 5,500 |
| Agonist Activity | Not detected | Not detected |
| Acute Antagonist Potency ($IC_{50(A)}$, nM) | >10,000 | 9,400 |
| Desensitization Potency ($IC_{50(D,10\,min)}$, nM) | 5 | 5,700 |

Example 4

ZW-87

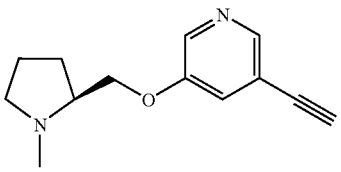

3-Ethynyl-5-(1-methyl-pyrrolidin-2-ylmethoxy)-pyridine

| Property | nAChR Subtype | |
|---|---|---|
| | α4β2 | α3β4 |
| Equilibrium binding affinity ($K_i$, nM) | 1.6 | 6,800 |
| Agonist Activity | Not detected | Not detected |

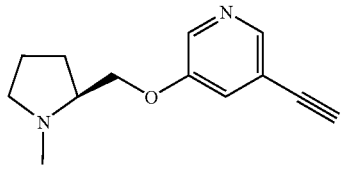

3-Ethynyl-5-(1-methyl-pyrrolidin-2-ylmethoxy)-pyridine

| Property | nAChR Subtype | |
|---|---|---|
| | α4β2 | α3β4 |
| Acute Antagonist Potency ($IC_{50(A)}$, nM) | >10,000 | >10,000 |
| Desensitization Potency ($IC_{50(D,10\,min)}$, nM) | 50 | >10,000 |

Example 5

ZW-88

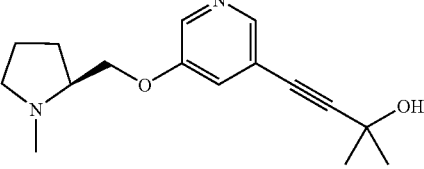

2-Methyl-4-[5-(1-methyl-pyrrolidin-2-ylmethoxy)-pyridin-3-yl]-but-3-yn-2-ol

| Property | nAChR Subtype | |
|---|---|---|
| | α4β2 | α3β4 |
| Equilibrium binding affinity ($K_i$, nM) | 2.9 | 61,000 |
| Agonist Activity | Not detected | Not detected |
| Acute Antagonist Potency ($IC_{50(A)}$, nM) | >10,000 | >10,000 |
| Desensitization Potency ($IC_{50(D,10\,min)}$, nM) | 890 | >10,000 |

Example 6

ZW-89

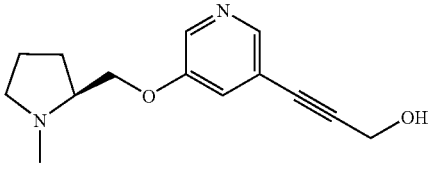

3-[5-(1-Methyl-pyrrolidin-2-ylmethoxy)-pyridin-3-yl]-prop-2-yn-1-ol

| Property | nAChR Subtype | |
|---|---|---|
| | α4β2 | α3β4 |
| Equilibrium binding affinity ($K_i$, nM) | 0.93 | 23,000 |
| Agonist Activity | Not detected | Not detected |
| Acute Antagonist Potency ($IC_{50(A)}$, nM) | >10,000 | >10,000 |
| Desensitization Potency ($IC_{50(D,10\,min)}$, nM) | 180 | >10,000 |

Example 7

ZW-91

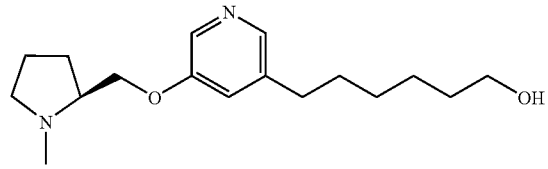

6-[5-(1-Methyl-pyrrolidin-2-ylmethoxy)-pyridin-3-yl]-hexan-1-ol

| Property | nAChR Subtype | |
|---|---|---|
| | α4β2 | α3β4 |
| Equilibrium binding affinity ($K_i$, nM) | 0.75 | 20,000 |
| Agonist Activity | Not detected | Not detected |
| Acute Antagonist Potency ($IC_{50(A)}$, nM) | >10,000 | >10,000 |
| Desensitization Potency ($IC_{50(D, 10\ min)}$, nM) | 1,000 | >10,000 |

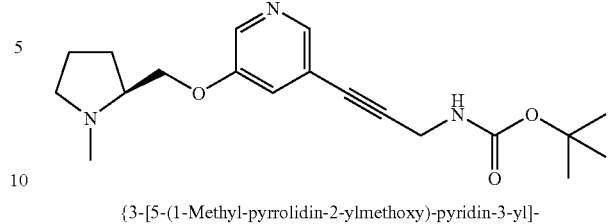

{3-[5-(1-Methyl-pyrrolidin-2-ylmethoxy)-pyridin-3-yl]-prop-2-ynyl}-carbamic acid tert-butyl ester

| Property | nAChR Subtype | |
|---|---|---|
| | α4β2 | α3β4 |
| Acute Antagonist Potency ($IC_{50(A)}$, nM) | >10,000 | >10,000 |
| Desensitization Potency ($IC_{50(D, 10\ min)}$, nM) | 22 | 6,900 |

Example 8

ZW-93

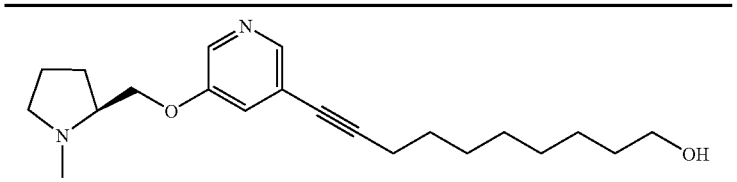

10-[5-(1-Methyl-pyrrolidin-2-ylmethoxy)-pyridin-3-yl]-dec-9-yn-1-ol

| Property | nAChR Subtype | |
|---|---|---|
| | α4β2 | α3β4 |
| Equilibrium binding affinity ($K_i$, nM) | 6.1 | 66,000 |
| Agonist Activity | Not detected | Not detected |
| Acute Antagonist Potency ($IC_{50(A)}$, nM) | 7,400 | 4,600 |
| Desensitization Potency ($IC_{50(D, 10\ min)}$, nM) | 460 | 3,800 |

Example 9

ZW-97

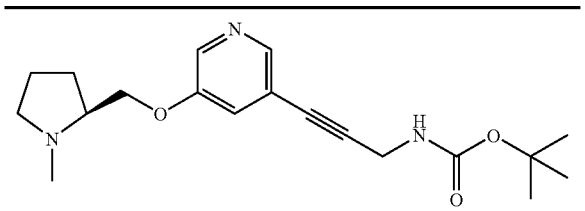

{3-[5-(1-Methyl-pyrrolidin-2-ylmethoxy)-pyridin-3-yl]-prop-2-ynyl}-carbamic acid tert-butyl ester

| Property | nAChR Subtype | |
|---|---|---|
| | α4β2 | α3β4 |
| Equilibrium binding affinity ($K_i$, nM) | 1.4 | 75,000 |
| Agonist Activity | Not detected | Not detected |

Example 10

ZW-98

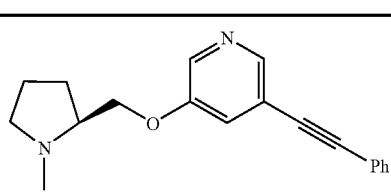

3-(1-Methyl-pyrrolidin-2-ylmethoxy)-5-phenylethynyl-pyridine

| Property | nAChR Subtype | |
|---|---|---|
| | α4β2 | α3β4 |
| Equilibrium binding affinity ($K_i$, nM) | 0.51 | 8,100 |
| Agonist Activity | Not detected | Not detected |

-continued

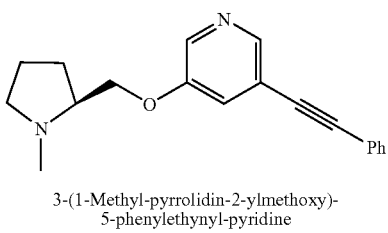 [SMILES: CN1CCC[C@H]1COc1cncc(C#Cc2ccccc2)c1]

3-(1-Methyl-pyrrolidin-2-ylmethoxy)-
5-phenylethynyl-pyridine

| Property | nAChR Subtype | |
|---|---|---|
| | α4β2 | α3β4 |
| Acute Antagonist Potency (IC$_{50(A)}$, nM) | >10,000 | >10,000 |
| Desensitization Potency (IC$_{50(D,\ 10\ min)}$, nM) | 170 | 5,300 |

Example 11

ZW-100

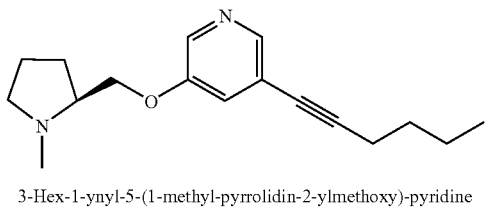 [SMILES: CCCCC#Cc1cncc(OC[C@@H]2CCCN2C)c1]

3-Hex-1-ynyl-5-(1-methyl-pyrrolidin-2-ylmethoxy)-pyridine

| Property | nAChR Subtype | |
|---|---|---|
| | α4β2 | α3β4 |
| Equilibrium binding affinity (K$_i$, nM) | 1.4 | 40,000 |
| Agonist Activity | Not detected | Not detected |
| Acute Antagonist Potency (IC$_{50(A)}$, nM) | >10,000 | >10,000 |
| Desensitization Potency (IC$_{50(D,\ 10\ min)}$, nM) | 190 | 3,300 |

Example 12

ZW-109

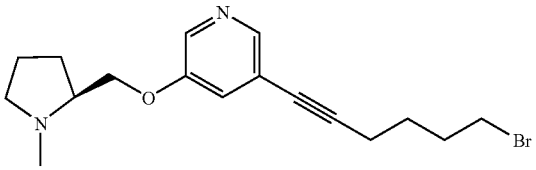

3-(6-Bromo-hex-1-ynyl)-5-(1-methyl-
pyrrolidin-2-ylmethoxy)-pyridine

| Property | nAChR Subtype | |
|---|---|---|
| | α4β2 | α3β4 |
| Equilibrium binding affinity (K$_i$, nM) | 1.4 | 16,000 |
| Agonist Activity | Not detected | Not detected |
| Acute Antagonist Potency (IC$_{50(A)}$, nM) | >10,000 | 6,900 |
| Desensitization Potency (IC$_{50(D,\ 10\ min)}$, nM) | 270 | 2,300 |

Example 13

ZW-110

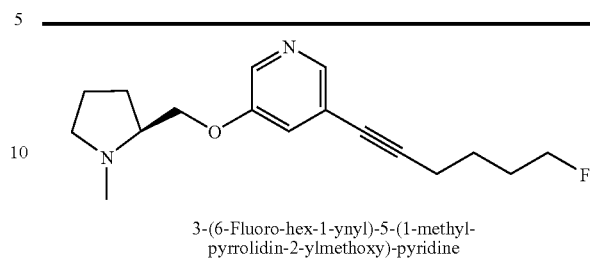

3-(6-Fluoro-hex-1-ynyl)-5-(1-methyl-
pyrrolidin-2-ylmethoxy)-pyridine

| Property | nAChR Subtype | |
|---|---|---|
| | α4β2 | α3β4 |
| Equilibrium binding affinity (K$_i$, nM) | 0.95 | 88,000 |
| Agonist Activity | Not detected | Not detected |
| Acute Antagonist Potency (IC$_{50(A)}$, nM) | >10,000 | >10,000 |
| Desensitization Potency (IC$_{50(D,\ 10\ min)}$, nM) | 60 | >10,000 |

Example 14

ZW-101

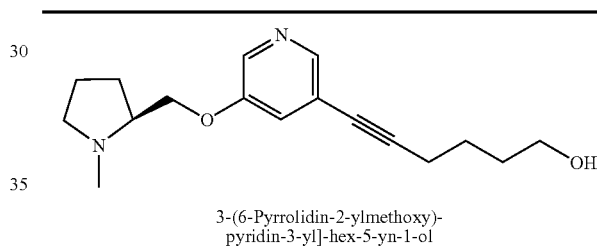

3-(6-Pyrrolidin-2-ylmethoxy)-
pyridin-3-yl]-hex-5-yn-1-ol

| Property | nAChR Subtype | |
|---|---|---|
| | α4β2 | α3β4 |
| Equilibrium binding affinity (K$_i$, nM) | 0.67 | 16,000 |
| Agonist Activity | Not detected | Not detected |
| Acute Antagonist Potency (IC$_{50(A)}$, nM) | >10,000 | >10,000 |
| Desensitization Potency (IC$_{50(D,\ 10\ min)}$, nM) | 160 | 2,500 |

Example 15

ZW-102

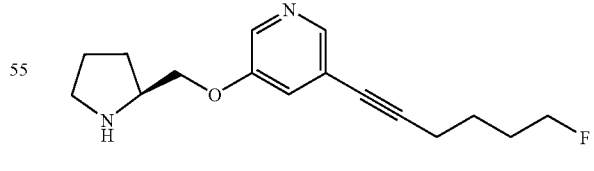

3-(6-Fluoro-hex-1-ynyl)-5-(pyrrolidin-
2-ylmethoxy)-pyridine

| Property | nAChR Subtype | |
|---|---|---|
| | α4β2 | α3β4 |
| Equilibrium binding affinity (K$_i$, nM) | 0.91 | 7,600 |
| Agonist Activity | Not detected | Not detected |

33

-continued

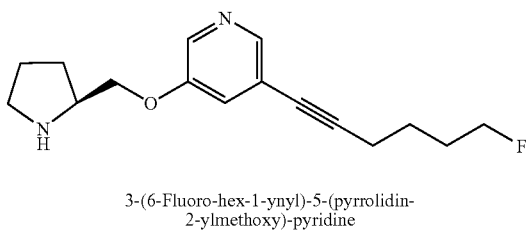 [SMILES: FCCCCC#Cc1cncc(OC[C@@H]2CCCN2)c1]

3-(6-Fluoro-hex-1-ynyl)-5-(pyrrolidin-2-ylmethoxy)-pyridine

| Property | nAChR Subtype | |
| --- | --- | --- |
| | α4β2 | α3β4 |
| Acute Antagonist Potency (IC$_{50(A)}$, nM) | >10,000 | >10,000 |
| Desensitization Potency (IC$_{50(D, 10\ min)}$, nM) | 120 | 5,400 |

Example 16

SKC-2-150

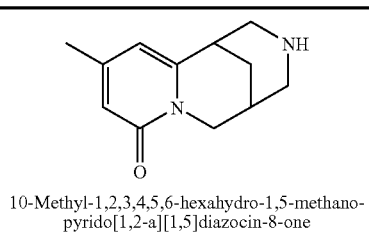

10-Methyl-1,2,3,4,5,6-hexahydro-1,5-methano-pyrido[1,2-a][1,5]diazocin-8-one

| Property | nAChR Subtype | |
| --- | --- | --- |
| | α4β2 | α3β4 |
| Equilibrium binding affinity (K$_i$, nM) | 1.9 | 6,700 |
| Agonist Activity | Not detected | Not detected |
| Acute Antagonist Potency (IC$_{50(A)}$, nM) | >10,000 | >10,000 |
| Desensitization Potency (IC$_{50(D, 10\ min)}$, nM) | 250 | >10,000 |

Example 17

SKC-2-203

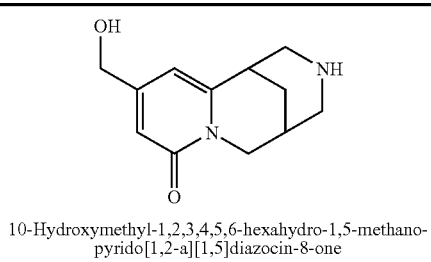

10-Hydroxymethyl-1,2,3,4,5,6-hexahydro-1,5-methano-pyrido[1,2-a][1,5]diazocin-8-one

| Property | nAChR Subtype | |
| --- | --- | --- |
| | α4β2 | α3β4 |
| Equilibrium binding affinity (K$_i$, nM) | 11 | 13,000 |
| Agonist Activity | Not detected | Not detected |
| Acute Antagonist Potency (IC$_{50(A)}$, nM) | >10,000 | >10,000 |
| Desensitization Potency (IC$_{50(D, 10\ min)}$, nM) | 600 | >10,000 |

34

Synthesis of Sazetidine-A

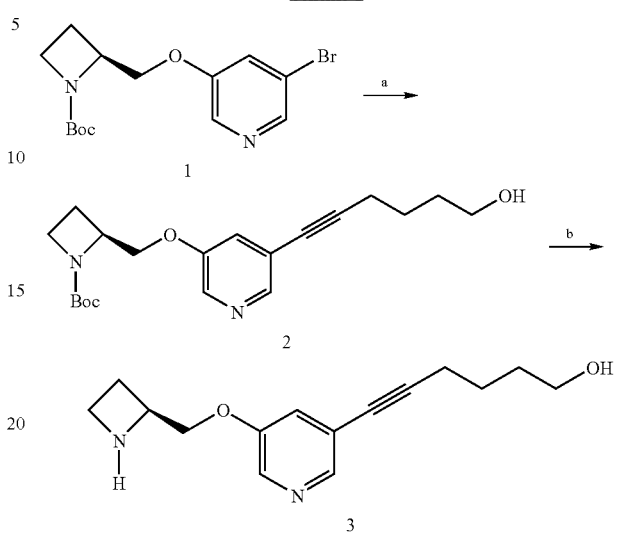

Scheme 1

Reagent: (a) 4-hexyn-1-ol, isopropylamine, copper(I) iodide, (PPh$_3$)$_2$PdCl$_2$, tri-t-butyl phosphine, 80° C., 36 h, 98%. (b) 1M HCl in Et$_2$O, 79%.

Sazetidine-A was synthesized from a precursor, (s)-5-bromo-3-{[1-(tert-butoxycarbonyl)-2-azetinyl]-methoxy}pyridine. This precursor was coupled with 5-hexyn-1-ol via palladium-catalyzed Sonogashira reaction at 80° C., in the presence of P(t-Bu)$_3$, to afford (s)-5-(5-hexyn-1-ol)-3-{[1-(tert-butoxycarbonyl)-2-azetidinyl]-methoxy}pyridine. The coupling product was then de-protected with 1 M HCl in diethyl ether to give 6-(5-(((S)-azetidin-2-yl)methoxy)pyridin-3-yl)hex-5-yn-1-ol (sazetidine-A).

(s)-5-(5-Hexyn-1-ol)-3-{[1-(tert-butoxycarbonyl)-2-azetidinyl]-methoxy}pyridine

To a v-vial containing of (s)-5-bromo-3-{[1-(tert-butoxycarbonyl)-2-azetinyl]-methoxy}pyridine (60 mg, 0.17 mmol) was added a solution of 5-hexyn-1-ol (0.022 mL, 0.2 mmol) in isopropylamine (1 mL), followed by charging with copper (I) iodide (3.3 mg, 0.017 mmol), (PPh$_3$)$_2$PdCl$_2$ (3.7 mg, 0.0085 mmol), and tri-tert-butly phosphine (10% in hexane, 22.5 mg, 0.011 mmol). The mixture was heated at 80° C. for 36 h. The solution was cooled, diluted with EtOAc (5 mL), filtered through a small pad of silica gel, and concentrated. The residue was purified by flush chromatography using ethyl acetate/dichloromethane (2:3) to give 60 mg (81%) of desired product. $^1$H NMR (CDCl$_3$, δ) 1.42 (s, 9H), 1.68-1.78 (m, 4H), 2.22-2.40 (m, 2H), 2.47 (t, J=6 Hz, 2H), 3.70 (t, J=5.6 Hz, 2H), 3.88 (t, J=7.2 Hz, 2H), 4.11 (dd, J$_1$=10, J$_2$=2.8 Hz, 2H), 4.41 (m, 1H), 7.48 (m, 1H), 7.62 (m, 2H). FAM-HRMS: calculated for C$_{20}$H$_{28}$N$_2$O$_4$: 360.4473; found: 361.2132 (M+H)$^+$.

(s)-5-(5-Hexyn-1-ol)-3-(2-azetidinylmethoxy)pyridine

To an ethanolic solution (0.2 mL) of (s)-5-(5-Hexyn-1-ol)-3-{[1-(tert-butoxycarbonyl)-2-azetidinyl]-methoxy}pyridine (20 mg, 56 μmol), was added 1 mL of 1 M HCl in anhydrous diethyl ether. The reaction was allowed to proceed for 12 h before collection the resulting white precipitate via suction filtration and washing with ice-cold diethyl ether. Desired product (15 mg, 78%) was obtained. $^1$H NMR (CD$_3$OD, δ) 1.71 (m, 4H), 2.56 (m, 2H), 2.69 (t, J=8.0 Hz, 2H), 3.60 (t, J=2.8 Hz, 2H), 4.10 (m, 2H), 4.55 (m, 2H), 4.82 (m, 1H), 8.21 (m, 1H), 8.59 (m, 2H). FAM-HRMS: calculated for C$_{15}$H$_{20}$N$_2$O$_2$: 260.1525; found: 261.1613 (M+H)$^+$.

The synthesis of Sazetidine-A as described above is for illustrative purpose. It is understood by one skilled in the art that other examples can be prepared using procedures analogous to the synthesis of Sazetidine-A without undue experimentation.

While the present invention has been particularly shown and described with respect to preferred embodiments thereof, it will be understood by those skilled in the art that the foregoing and other changes in forms and details may be made without departing from the spirit and scope of the invention. It is therefore intended that the present invention not be limited to the exact forms and details described and illustrated but fall within the scope of the appended claims.

REFERENCES

Alkondon, M., and Albuquerque, E. X. (2004). The nicotinic acetylcholine receptor subtypes and their function in the hippocampus and cerebral cortex. Prog Brain Res 145, 109-120.

Bertrand, D., Ballivet, M., and Rungger, D. (1990). Activation and blocking of neuronal nicotinic acetylcholine receptor reconstituted in *Xenopus oocytes*. Proc Natl Acad Sci USA 87, 1993-1997.

Brody, A. L., Mandelkern, M. A., London, E. D., Olmstead, R. E., Farahi, J., Scheibal, D., Jou, J., Allen, V., Tiongson, E., Chefer, S. I., et al. (2006). Cigarette smoking saturates brain alpha 4 beta 2 nicotinic acetylcholine receptors. Arch Gen Psychiatry 63, 907-915.

Cassels, B. K., Bermudez, I., Dajas, F., Abin-Carriquiry, J. A., and Wonnacott, S. (2005). From ligand design to therapeutic efficacy: the challenge for nicotinic receptor research. Drug Discov Today 10, 1657-1665.

Changeux, J. P., and Edelstein, S. J. (1998). Allosteric receptors after 30 years. Neuron 21, 959-980.

Changeux, J. P., and Edelstein, S. J. (2005). Allosteric mechanisms of signal transduction. Science 308, 1424-1428.

Colquhoun, D., and Sakmann, B. (1998). From muscle endplate to brain synapses: a short history of synapses and agonist-activated ion channels. Neuron 20, 381-387.

Daly, J. W. (2005). Nicotinic agonists, antagonists, and modulators from natural sources. Cell Mol Neurobiol 25, 513-552.

Dani, J. A., and Bertrand, D. (2007). Nicotinic Acetylcholine Receptors and Nicotinic Cholinergic Mechanisms of the Central Nervous System. Annu Rev Pharmacol Toxicol 47, 699-729.

Dani, J. A., and Harris, R. A. (2005). Nicotine addiction and comorbidity with alcohol abuse and mental illness. Nat Neurosci 8, 1465-1470.

De Biasi, M. (2002). Nicotinic receptor mutant mice in the study of autonomic function. Curr Drug Targets CNS Neurol Disord 1, 331-336.

Di Chiara, G. (2000). Role of dopamine in the behavioural actions of nicotine related to addiction. Eur J Pharmacol 393, 295-314.

Eaton, J. B., Peng, J. H., Schroeder, K. M., George, A. A., Fryer, J. D., Krishnan, C., Buhlman, L., Kuo, Y. P., Steinlein, O., and Lukas, R. J. (2003). Characterization of human alpha 4 beta 2-nicotinic acetylcholine receptors stably and heterologously expressed in native nicotinic receptor-null SH-EP1 human epithelial cells. Mol Pharmacol 64, 1283-1294.

Fitch, R. W., Xiao, Y., Kellar, K. J., and Daly, J. W. (2003). Membrane potential fluorescence: a rapid and highly sensitive assay for nicotinic receptor channel function. Proc Natl Acad Sci USA 100, 4909-4914.

Flores, C. M., DeCamp, R. M., Kilo, S., Rogers, S. W., and Hargreaves, K. M. (1996). Neuronal nicotinic receptor expression in sensory neurons of the rat trigeminal ganglion: demonstration of alpha3beta4, a novel subtype in the mammalian nervous system. J Neurosci 16, 7892-7901.

Flores, C. M., Rogers, S. W., Pabreza, L. A., Wolfe, B. B., and Kellar, K. J. (1992). A subtype of nicotinic cholinergic receptor in rat brain is composed of alpha 4 and beta 2 subunits and is up-regulated by chronic nicotine treatment. Mol Pharmacol 41, 31-37.

Gahring, L. C., and Rogers, S. W. (2005). Neuronal nicotinic acetylcholine receptor expression and function on nonneuronal cells. Aaps J 7, E885-894.

Ghosheh, O. A., Dwoskin, L. P., Miller, D. K., and Crooks, P. A. (2001). Accumulation of nicotine and its metabolites in rat brain after intermittent or continuous peripheral administration of [2'-(14)C]nicotine. Drug Metab Dispos 29, 645-651.

Giniatullin, R., Nistri, A., and Yakel, J. L. (2005). Desensitization of nicotinic ACh receptors: shaping cholinergic signaling. Trends Neurosci 28, 371-378.

Gotti, C., and Clementi, F. (2004). Neuronal nicotinic receptors: from structure to pathology. Prog Neurobiol 74, 363-396.

Gotti, C., Zoli, M., and Clementi, F. (2006). Brain nicotinic acetylcholine receptors: native subtypes and their relevance. Trends Pharmacol Sci 27, 482-491.

Gourlay, S. G., and Benowitz, N. L. (1997). Arteriovenous differences in plasma concentration of nicotine and catecholamines and related cardiovascular effects after smoking, nicotine nasal spray, and intravenous nicotine. Clin Pharmacol Ther 62, 453-463.

Henningfield, J. E., Stapleton, J. M., Benowitz, N. L., Grayson, R. F., and London, E. D. (1993). Higher levels of nicotine in arterial than in venous blood after cigarette smoking. Drug Alcohol Depend 33, 23-29.

Hogg, R. C., and Bertrand, D. (2007). Partial agonists as therapeutic agents at neuronal nicotinic acetylcholine receptors. Biochem Pharmacol 73, 459-468.

Hulihan-Giblin, B. A., Lumpkin, M. D., and Kellar, K. J. (1990). Acute effects of nicotine on prolactin release in the rat: agonist and antagonist effects of a single injection of nicotine. J Pharmacol Exp Ther 252, 15-20.

Jain, K. K. (2004). Modulators of nicotinic acetylcholine receptors as analgesics. Curr Opin Investig Drugs 5, 76-81.

Jensen, A. A., Frolund, B., Liljefors, T., and Krogsgaard-Larsen, P. (2005). Neuronal nicotinic acetylcholine receptors: structural revelations, target identifications, and therapeutic inspirations. J Med Chem 48, 4705-4745.

Karlin, A. (1967). On the application of "a plausible model" of allosteric proteins to the receptor for acetylcholine. J Theor Biol 16, 306-320.

Karlin, A. (2002). Emerging structure of the nicotinic acetylcholine receptors. Nat Rev Neurosci 3, 102-114.

Katz, B., and Thesleff, S. (1957). A study of the desensitization produced by acetylcholine at the motor end-plate. J Physiol 138, 63-80.

Kellar, K. J. (2006). Overcoming inhibitions. Proc Natl Acad Sci USA 103, 13263-13264.

Kellar, K. J., Davila-Garcia, M. I., and Xiao, Y. (1999). Pharmacology of neuronal nicotinic acetylcholine recceptors: effects of acute and chronic nicotine. Nicotine Tob Res 1 Suppl 2, S117-120; discussion S139-140.

Kellar, K. J., and Xiao, Y. (2007). Neuronal nicotinic receptors: one hundred years of progress. In Hand book of Contemparary Neuropharmacology, D. R. Sibley, I. Hanin, M. Kuhar, and P. Skolnick, eds. (New Jersey, John Wiley & Sons, Inc.), pp. 107-146.

Kuryatov, A., Luo, J., Cooper, J., and Lindstrom, J. (2005). Nicotine acts as a pharmacological chaperone to up-regulate human alpha4beta2 acetylcholine receptors. Mol Pharmacol 68, 1839-1851.

Langley, J. N. (1905). On the reaction of cells and of nerve-endings to certain poisons, chiefly as regards the reaction of striated muscle to nicotine and to curari. J Physiol 33, 374-413.

Langley, J. N. (1907). On the contraction of muscle, chiefly in relation to the presence of "receptive" substances. Journal of Physiology (London) 37, 347-384.

Langley, J. N., and Dickenson, W. (1889). On the local paralysis of peripheral ganglia and on the connexion of different classes of nerve fibres with them. Proc RoySoc 46, 423-431.

Laviolette, S. R., and van der Kooy, D. (2004). The neurobiology of nicotine addiction: bridging the gap from molecules to behaviour. Nat Rev Neurosci 5, 55-65.

Le Novere, N., Corringer, P. J., and Changeux, J. P. (2002). The diversity of subunit composition in nAChRs: evolutionary origins, physiologic and pharmacologic consequences. J Neurobiol 53, 447-456.

Lester, H. A., Dibas, M. I., Dahan, D. S., Leite, J. F., and Dougherty, D. A. (2004). Cys-loop receptors: new twists and turns. Trends Neurosci 27, 329-336.

Levin, E. D., McClernon, F. J., and Rezvani, A. H. (2006). Nicotinic effects on cognitive function: behavioral characterization, pharmacological specification, and anatomic localization. Psychopharmacology (Berl) 184, 523-539.

Lindstrom, J. (1996). Neuronal nicotinic acetylcholine receptors. Ion Channels 4, 377-450.

Lindstrom, J. (1997). Nicotinic acetylcholine receptors in health and disease. Mol Neurobiol 15, 193-222.

Lindstrom, J. M. (2002). Acetylcholine receptor structure. In Current Clinical Neurology: Myasthenia Gravis and Related Disorders, H. J. Kaminski, ed. (New York, Human Press), pp. 15-52.

Lu, Y., Marks, M. J., and Collins, A. C. (1999). Desensitization of nicotinic agonist-induced [3H]gamma-aminobutyric acid release from mouse brain synaptosomes is produced by subactivating concentrations of agonists. J Pharmacol Exp Ther 291, 1127-1134.

Lukas, R. J., Changeux, J. P., Le Novere, N., Albuquerque, E. X., Balfour, D. J., Berg, D. K., Bertrand, D., Chiappinelli, V. A., Clarke, P. B., Collins, A. C., et al. (1999). International Union of Pharmacology. XX. Current status of the nomenclature for nicotinic acetylcholine receptors and their subunits. Pharmacol Rev 51, 397-401.

Mansvelder, H. D., and McGehee, D. S. (2002). Cellular and synaptic mechanisms of nicotine addiction. J Neurobiol 53, 606-617.

Marubio, L. M., Gardier, A. M., Durier, S., David, D., Klink, R., Arroyo-Jimenez, M. M., McIntosh, J. M., Rossi, F., Champtiaux, N., Zoli, M., and Changeux, J. P. (2003). Effects of nicotine in the dopaminergic system of mice lacking the alpha4 subunit of neuronal nicotinic acetylcholine receptors. Eur J Neurosci 17, 1329-1337.

Maskos, U., Molles, B. E., Pons, S., Besson, M., Guiard, B. P., Guilloux, J. P., Evrard, A., Cazala, P., Cormier, A., Mameli-Engvall, M., et al. (2005). Nicotine reinforcement and cognition restored by targeted expression of nicotinic receptors. Nature 436, 103-107.

Mihalak, K. B., Carroll, F. I., and Luetje, C. W. (2006). Varenicline is a partial agonist at alpha4beta2 and a full agonist at alpha7 neuronal nicotinic receptors. Mol Pharmacol 70, 801-805.

Millar, N. S. (2003). Assembly and subunit diversity of nicotinic acetylcholine receptors. Biochem Soc Trans 31, 869-874.

Nestler, E. J. (2005). Is there a common molecular pathway for addiction? Nat Neurosci 8, 1445-1449.

Paterson, D., and Nordberg, A. (2000). Neuronal nicotinic receptors in the human brain. Prog Neurobiol 61, 75-111.

Picciotto, M. R., Zoli, M., Rimondini, R., Lena, C., Marubio, L. M., Pich, E. M., Fuxe, K., and Changeux, J. P. (1998). Acetylcholine receptors containing the beta2 subunit are involved in the reinforcing properties of nicotine. Nature 391, 173-177.

Pidoplichko, V. I., Noguchi, J., Areola, O. O., Liang, Y., Peterson, J., Zhang, T., and Dani, J. A. (2004). Nicotinic cholinergic synaptic mechanisms in the ventral tegmental area contribute to nicotine addiction. Learn Mem 11, 60-69.

Quick, M. W., and Lester, R. A. (2002). Desensitization of neuronal nicotinic receptors. J Neurobiol 53, 457-478.

Rollema, H., Coe, J. W., Chambers, L. K., Hurst, R. S., Stahl, S. M., and Williams, K. E. (2007). Rationale, pharmacology and clinical efficacy of partial agonists of alpha(4)beta(2) nACh receptors for smoking cessation. Trends Pharmacol Sci 28, 316-325.

Sharp, B. M., and Beyer, H. S. (1986). Rapid desensitization of the acute stimulatory effects of nicotine on rat plasma adrenocorticotropin and prolactin. J Pharmacol Exp Ther 238, 486-491.

Sine, S. M., and Engel, A. G. (2006). Recent advances in Cys-loop receptor structure and function. Nature 440, 448-455.

Skok, V. I. (2002). Nicotinic acetylcholine receptors in autonomic ganglia. Auton Neurosci 97, 1-11.

Tapper, A. R., McKinney, S. L., Nashmi, R., Schwarz, J., Deshpande, P., Labarca, C., Whiteaker, P., Marks, M. J., Collins, A. C., and Lester, H. A. (2004). Nicotine activation of alpha4* receptors: sufficient for reward, tolerance, and sensitization. Science 306, 1029-1032.

Unwin, N. (2005). Refined structure of the nicotinic acetylcholine receptor at 4 A resolution. J Mol Biol 346, 967-989.

Wang, H., and Sun, X. (2005). Desensitized nicotinic receptors in brain. Brain Res Brain Res Rev 48, 420-437.

Wang, N., Orr-Urtreger, A., and Korczyn, A. D. (2002). The role of neuronal nicotinic acetylcholine receptor subunits in autonomic ganglia: lessons from knockout mice. Prog Neurobiol 68, 341-360.

Webster, J. C., Francis, M. M., Porter, J. K., Robinson, G., Stokes, C., Horenstein, B., and Papke, R. L. (1999). Antagonist activities of mecamylamine and nicotine show reciprocal dependence on beta subunit sequence in the second transmembrane domain. Br J Pharmacol 127, 1337-1348.

Whiting, P., and Lindstrom, J. (1987). Purification and characterization of a nicotinic acetylcholine receptor from rat brain. Proc Natl Acad Sci USA 84, 595-599.

Wonnacott, S., Barik, J., Dickinson, J., and Jones, I. W. (2006). Nicotinic receptors modulate transmitter cross talk in the CNS: nicotinic modulation of transmitters. J Mol Neurosci 30, 137-140.

Xiao, Y., Fan, H., Musachio, J. L., Wei, Z. L., Chellappan, S. K., Kozikowski, A. P., and Kellar, K. J. (October, 2006). Sazetidine-A, a novel ligand that desensitizes alpha4beta2 nicotinic acetylcholine receptors without activating them. Mol Pharmacol 70, 1454-1460.

Xiao, Y., and Kellar, K. J. (2004). The comparative pharmacology and up-regulation of rat neuronal nicotinic receptor subtype binding sites stably expressed in transfected mammalian cells. J Pharmacol Exp Ther 310, 98-107.

Xiao, Y., Meyer, E. L., Thompson, J. M., Surin, A., Wroblewski, J., and Kellar, K. J. (1998). Rat alpha3/beta4 subtype of neuronal nicotinic acetylcholine receptor stably expressed in a transfected cell line: pharmacology of ligand binding and function. Mol Pharmacol 54, 322-333.

Zhou, F. M., Wilson, C. J., and Dani, J. A. (2002). Cholinergic interneuron characteristics and nicotinic properties in the striatum. J Neurobiol 53, 590-605.

We claim:

1. A pharmaceutical composition comprising a compound of formula (I):

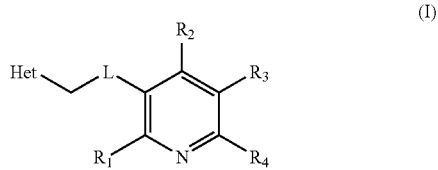

or a pharmaceutically acceptable tautomer, salt, or solvate thereof; and a pharmaceutically acceptable carrier or excipient;

wherein,

L is O, S, or $NR^5$;

Het is heterocyclyl;

each $R^2$ and $R^4$, is independently H, halo, amino, N-alkyl amino, N,N-dialkyl amino, amido, nitro, cyano, hydroxyl, alkoxy, or an optionally substituted $C_1$-$C_{12}$ alkyl, $C_2$-$C_{12}$ alkenyl, or $C_2$-$C_{12}$ alkynyl, wherein the substituents are selected from the group consisting of hydroxyl, halo, amino, N-alkyl amino, N,N-dialkyl amino, —NH—C(O)—$R^6$, —NH—C(O)—$OR^6$, —O—C(O)—$R^6$, —O—C(O)—$OR^6$, nitro, and alkoxy;

$R^1$ is halo, amino, N-alkyl amino, N,N-dialkyl amino, amido, nitro, cyano, hydroxyl, alkoxy, or an optionally substituted $C_1$-$C_{12}$ alkyl, $C_2$-$C_{12}$ alkenyl, or $C_2$-$C_{12}$ alkynyl, wherein the substituents are selected from the group consisting of hydroxyl, halo, amino, N-alkyl amino, N,N-dialkyl amino, —NH—C(O)—$R^6$, —NH—C(O)—$OR^6$, —O—C(O)—$R^6$, —O—C(O)—$OR^6$, nitro, and alkoxy;

$R^3$ is an optionally substituted $C_2$-$C_{12}$ alkenyl, or $C_2$-$C_{12}$ alkynyl, wherein the substituents are selected from the group consisting of hydroxyl, halo, amino, N-alkyl amino, N,N-dialkyl amino, —NH—C(O)—$R^6$, —NH—C(O)—$OR^6$, —O—C(O)—$R^6$, —O—C(O)—$OR^6$, nitro, and alkoxy;

$R^5$ is H, or an optionally substituted $C_1$-$C_6$ alkyl, $C_2$-$C_6$ alkenyl, or $C_2$-$C_6$ alkynyl; and $R^6$ is an optionally substituted $C_1$-$C_6$ alkyl, $C_2$-$C_6$ alkenyl, $C_2$-$C_6$ alkynyl, aryl, or heteroaryl.

2. The pharmaceutical composition of claim 1, further comprising at least one additional active agent.

3. The pharmaceutical composition of claim 1, wherein $R^1$ is halo, amino, N-alkyl amino, N,N-dialkyl amino, amido, nitro, cyano, hydroxyl, or alkoxy, or an optionally substituted $C_1$-$C_{12}$ alkyl, $C_2$-$C_{12}$ alkenyl, or $C_2$-$C_{12}$ alkynyl; and $R^2$ and $R^4$ are H.

4. The pharmaceutical composition of claim 1, wherein $R^3$ is an optionally substituted $C_2$-$C_{12}$ alkynyl.

5. The pharmaceutical composition of claim 1, wherein Het is a 4- to 7-membered monocyclic fully-saturated heterocyclic ring containing at least one hetero atom selected from the group consisting of N, O, and S.

6. The pharmaceutical composition of claim 1, wherein $R^1$ is halo, amino, N-alkyl amino, N,N-dialkyl amino, amido, nitro, cyano, hydroxyl, or alkoxy, or an optionally substituted $C_1$-$C_{12}$ alkyl, $C_2$-$C_{12}$ alkenyl, or $C_2$-$C_{12}$ alkynyl, wherein the substituents are selected from the group consisting of hydroxyl, halo, amino, N-alkyl amino, N,N-dialkyl amino, —NH—C(O)—$R^6$, —NH—C(O)—$OR^6$, —O—C(O)—$R^6$, —O—C(O)—$OR^6$, nitro, and alkoxy;

$R^2$ and $R^4$ are H;

$R^3$ is an optionally substituted $C_2$-$C_{12}$ alkynyl; and

Het is a 4- to 7-membered monocyclic fully-saturated heterocyclic ring containing at least one hetero atom selected from the group consisting of N, O, and S.

7. A compound of formula (I):

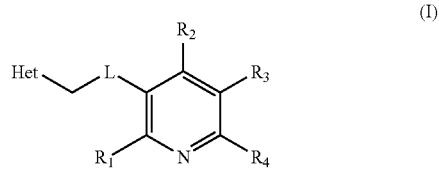

or a pharmaceutically acceptable tautomer, salt, or solvate thereof; wherein,

L is O, S, or $NR^5$;

Het is heterocyclyl;

each $R^2$ and $R^4$ is independently H, halo, amino, N-alkyl amino, N,N-dialkyl amino, amido, nitro, cyano, hydroxyl, alkoxy, or an optionally substituted $C_1$-$C_{12}$ alkyl, $C_2$-$C_{12}$ alkenyl, or $C_2$-$C_{12}$ alkynyl, wherein the substituents are selected from the group consisting of hydroxyl, halo, amino, N-alkyl amino, N,N-dialkyl amino, —NH—C(O)—$R^6$, —NH—C(O)—$OR^6$, —O—C(O)—$R^6$, —O—C(O)—$OR^6$, nitro, and alkoxy;

$R^1$ is halo, amino, N-alkyl amino, N,N-dialkyl amino, amido, nitro, cyano, or an optionally substituted $C_1$-$C_{12}$ alkyl, $C_2$-$C_{12}$ alkenyl, or $C_2$-$C_{12}$ alkynyl, wherein the substituents are selected from the group consisting of hydroxyl, halo, amino, N-alkyl amino, N,N-dialkyl amino, —NH—C(O)—$R^6$, —NH—C(O)—$OR^6$, —O—C(O)—$R^6$, —O—C(O)—$OR^6$, nitro, and alkoxy;

$R^3$ is an optionally substituted $C_1$-$C_{12}$ alkyl, $C_2$-$C_{12}$ alkenyl, or $C_2$-$C_{12}$ alkynyl, wherein the substituents are selected from the group consisting of hydroxyl, halo, amino, N-alkyl amino, N,N-dialkyl amino, —NH—C(O)—$R^6$, —NH—C(O)—$OR^6$, —O—C(O)—$R^6$, —O—C(O)—$OR^6$, nitro, and alkoxy;

R$^5$ is H, or an optionally substituted C$_1$-C$_6$ alkyl, C$_2$-C$_6$ alkenyl, or C$_2$-C$_6$ alkynyl; and R$^6$ is an optionally substituted C$_1$-C$_6$ alkyl, C$_2$-C$_6$ alkenyl, C$_2$-C$_6$ alkynyl, aryl, or heteroaryl.

8. The compound of claim 7, wherein R$^1$ is halo, amino, N-alkyl amino, N,N-dialkyl amino, amido, nitro, cyano, or an optionally substituted C$_1$-C$_{12}$ alkyl, C$_2$-C$_{12}$ alkenyl, or C$_2$-C$_{12}$ alkynyl, wherein the substituents are selected from the group consisting of hydroxyl, halo, amino, N-alkyl amino, N,N-dialkyl amino, —NH—C(O)—R$^6$, —NH—C(O)—OR$^6$, —O—C(O)—R$^6$, —O—C(O)—OR$^6$, nitro, and alkoxy; R$^2$ and R$^4$ are H.

9. The compound of claim 7, wherein R$^3$ is an optionally substituted C$_2$-C$_{12}$ alkynyl.

10. The compound of claim 7, wherein Het is a 4- to 7-membered monocyclic fully-saturated heterocyclic ring containing at least one hetero atom selected from the group consisting of N, O, and S.

11. The compound of claim 7, wherein

R$^1$ is halo, amino, N-alkyl amino, N,N-dialkyl amino, amido, nitro, cyano, or an optionally substituted C$_1$-C$_{12}$ alkyl, C$_2$-C$_{12}$ alkenyl, or C$_2$-C$_{12}$ alkynyl, wherein the substituents are selected from the group consisting of hydroxyl, halo, amino, N-alkyl amino, N,N-dialkyl amino, —NH—C(O)—R$^6$, —NH—C(O)—OR$^6$, —O—C(O)—R$^6$, —O—C(O)—OR$^6$, nitro, and alkoxy;

R$^2$ and R$^4$ are H;

R$^3$ is an optionally substituted C$_2$-C$_{12}$ alkynyl; and

Het is a 4- to 7-membered monocyclic fully-saturated heterocyclic ring containing at least one hetero atom selected from the group consisting of N, O, and S.

12. A compound of formula (I):

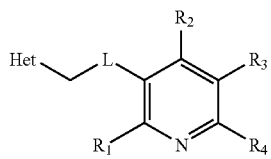

or a pharmaceutically acceptable tautomer, salt, solvate, or ester thereof; wherein, L is O;
Het is azetidinyl;
R$^1$, R$^2$, and R$^4$, are H;
R$^3$ is substituted C$_2$-C$_{12}$ alkynyl, wherein the substituent is —NH—C(O)—R$^6$, —NH—C(O)—OR$^6$, —O—C(O)—R$^6$, or —O—C(O)—OR$^6$; and
R$^6$ is an optionally substituted aryl or heteroaryl.

13. A compound of

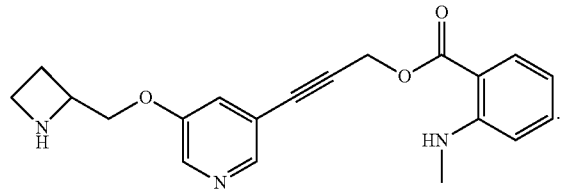 [SMILES: CNc1ccccc1C(=O)OCC#Cc1cncc(OCC2CCN2)c1]

14. A pharmaceutical composition comprising a compound of formula (I) as described in claim 12, or a pharmaceutically acceptable tautomer, salt, or solvate thereof; and a pharmaceutically acceptable carrier or excipient.

* * * * *

UNITED STATES PATENT AND TRADEMARK OFFICE
CERTIFICATE OF CORRECTION

PATENT NO. : 8,642,612 B2
APPLICATION NO. : 12/374172
DATED : February 4, 2014
INVENTOR(S) : Xiao et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1190 days.

Signed and Sealed this
Twelfth Day of May, 2015

Michelle K. Lee
*Director of the United States Patent and Trademark Office*